US010354347B2

(12) United States Patent
Hussam

(10) Patent No.: US 10,354,347 B2
(45) Date of Patent: Jul. 16, 2019

(54) GENERATING AND PROCESSING MEDICAL ALERTS FOR RE-ADMISSION REDUCTIONS

(71) Applicant: Ali Adel Hussam, Columbia, MO (US)

(72) Inventor: Ali Adel Hussam, Columbia, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 423 days.

(21) Appl. No.: 14/026,151

(22) Filed: Sep. 13, 2013

(65) Prior Publication Data
US 2015/0081314 A1    Mar. 19, 2015

(51) Int. Cl.
| | | |
|---|---|---|
| *G06Q 50/22* | (2018.01) | |
| *G06Q 10/10* | (2012.01) | |
| *G16H 10/20* | (2018.01) | |

(52) U.S. Cl.
CPC .............. *G06Q 50/22* (2013.01); *G06Q 10/10* (2013.01); *G16H 10/20* (2018.01)

(58) Field of Classification Search
CPC ........ G06Q 50/22; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | | |
|---|---|---|---|---|
| 6,532,281 B1* | 3/2003 | Schoenborn | .......... | H04M 15/00 379/114.01 |
| 6,697,696 B1* | 2/2004 | Hickey | ............ | G05B 19/41875 700/109 |
| 8,751,257 B2 | 6/2014 | Amland et al. | | |
| 2005/0273359 A1 | 12/2005 | Young | | |

(Continued)

FOREIGN PATENT DOCUMENTS

WO    WO2013098740    7/2013

OTHER PUBLICATIONS

International Search Report and Written Opinion in corresponding Application No. PCT/US2014/055340, dated Jan. 27, 2015, pp. 1-15.

*Primary Examiner* — Linh Giang Le
(74) *Attorney, Agent, or Firm* — Fish & Richardson P.C.

(57) ABSTRACT

A computer-implemented method includes accessing information indicative of a question to be answered by a medical patient, with the question being included in a medical assessment questionnaire of a medical service provider; receiving information indicative of a selection of one or more triggering events for answers to the question; and generating, for the question, a medical alert rule, with the medical alert rule comprising instructions to perform operations comprising: receiving an answer of the medical patient to the question; detecting, based on contents of the received answer, the triggering event for the question; and generating a medical questionnaire alert to notify the medical service provider that the medical patient has answered the question with the answer that is defined as being unacceptable.

12 Claims, 11 Drawing Sheets

(56) References Cited

U.S. PATENT DOCUMENTS

| | | |
|---|---|---|
| 2006/0004605 A1 | 1/2006 | Donoghue et al. |
| 2006/0235280 A1* | 10/2006 | Vonk ................... G06F 19/322 600/300 |
| 2008/0140449 A1* | 6/2008 | Hayes ................... G06Q 10/10 705/2 |
| 2011/0229867 A1 | 9/2011 | Gough et al. |
| 2012/0046965 A1* | 2/2012 | Ryan ................... G06F 19/3431 705/2 |
| 2013/0218951 A1 | 8/2013 | Scaletta |
| 2014/0118138 A1* | 5/2014 | Cobelli ................ A61B 5/0004 340/539.12 |

* cited by examiner

FIG. 2

GENERATING AND PROCESSING MEDICAL ALERTS FOR RE-ADMISSION REDUCTIONS

BACKGROUND

Generally, when a patient is released from a hospital and experiences a worsening of a condition, the patient is re-admitted to the hospital.

SUMMARY

In general, generating and processing medical alerts by a medical service provider for re-admission reduction is described. In an example, the medical service provider can be some combination of a hospital, a clinic, and one or more physicians, nurses, and other medical service professionals that provide medical care to one or more medical patients. In an example, a medical patient that has undergone a hip-replacement surgery can have a scheduled follow-up visit with the surgeon as part of the after-surgery recovery protocol. In an example, the follow-up visit is a routine visit, for example, periodically scheduled as part of the after-surgery recovery protocol. In another example, the follow-up visit may be in response to a particular occurrence of an event, such as a fever, fall, onset of pain, or for other reasons.

In one aspect of the present disclosure, a computer-implemented method includes accessing information indicative of a question to be answered by a medical patient, with the question being included in a medical assessment questionnaire of a medical service provider; receiving information indicative of a selection of one or more triggering events for answers to the question, with a triggering event specifying that the medical service provider has specified that a particular answer to the question is unacceptable and requires that the medical service provider be notified of the unacceptable answer; and generating, for the question, a medical alert rule, with the medical alert rule comprising instructions to perform operations comprising: receiving an answer of the medical patient to the question; detecting, based on contents of the received answer, the triggering event for the question; and generating, based on detection of the triggering event, a medical questionnaire alert to notify the medical service provider that the medical patient has answered the question with the answer that is defined as being unacceptable. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The actions include receiving the answer of the medical patient to the question; following receipt of the answer, executing the medical alert rule; detecting, based on contents of the answer and based on execution of the medical alert rule, the triggering event that the answer of the medical patient is unacceptable and requires that the medical service provider be notified of the unacceptable answer; and generating, based on detection of the triggering event, the medical questionnaire alert to notify the medical service provider that the medical patient has answered the question with the answer that is defined as being unacceptable. The actions include storing, in a data repository, the medical questionnaire alert in association with information that identifies the medical patient who is associated with the medical questionnaire alert. The medical patient comprises a first medical patient, and wherein the method further comprises: accessing appointment information for the medical service provider, with the accessed appointment information specifying one or more appointments that are scheduled with the medical service provider; for an appointment that is scheduled with the medical service provider, determining a second medical patient who is associated with the appointment; determining a generated medical questionnaire alerts for the second medical patient; using the accessed appointment information, generating information for an appointment graphical user interface that when rendered on a display device comprises: one or more first visual representations of the one or more appointments that are scheduled with the medical service provider; and a second visual representation of the generated medical questionnaire alert for the second medical patient; wherein the second visual representation is associated in the graphical user interface with the one of the one or more first visual representations that represents the appointment of the second medical patient, to alert the medical service provider that the second medical patient has an appointment with the medical service provider and that the second medical patient has a medical issue to be addressed by the medical service provider. The medical patient comprises a first medical patient, and wherein the method further comprises: accessing patient profile information for a second medical patient; identifying a medical questionnaire alert for the second medical patient; generating information for a patient profile graphical user interface that when rendered on a display device comprises: a first visual representation of the patient profile information; and a second visual representation of the identified medical questionnaire alert for the second medical patient and a status of the medical questionnaire alert, with the status specifying whether the alert is pending or resolved; wherein the second visual representation is juxtaposed to the first visual representation in the patient profile graphical user interface. The actions include accessing information indicative of a plurality of medical questionnaire alerts for the medical service provider; aggregating the plurality of medical questionnaire alerts together; generating information for an alert management graphical user interface that when rendered on a display device comprises: visual representations of the aggregated plurality of medical questionnaire alerts.

In another aspect of the disclosure, a computer-implemented method includes transmitting, to a client computing device associated with a user, information indicative of a risk factor questionnaire, with the risk factor questionnaire comprising a plurality of questions regarding risk factors of a medical procedure performed on the user; periodically receiving, from the client computing device, information indicative of answers to the plurality of questions regarding the risk factors of the medical procedure; analyzing, by one or more processing devices and over a predefined period of time, the information that is periodically received; detecting, by the one or more processing devices and based on analyzing, that the user is at risk of readmission to a medical facility; generating, by the one or more processing devices, an action to be performed by a member of the medical facility, with performance of the action reducing the risk of readmission relative to other risks of readmission that are independent of performance of the action; and transmitting, to a client computing device associated with the medical facility, an alert of the generated action to promote the member of the medical facility to perform the action. Other embodiments of this aspect include corresponding computer systems, apparatus, and computer programs recorded on one or more computer storage devices, each configured to perform the actions of the methods.

In some implementations, the method includes detecting, by the one or more processing devices and based on analyzing, that the user is at risk of readmission to a medical facility comprises: detecting an increase in a severity of a medical condition of the user during one or more time intervals in predefined period of time, relative to a severity of the medical condition during other time intervals in the predefined period of time. The actions include determining that the detected increase exceeds a threshold level; and wherein detecting, by the one or more processing devices and based on analyzing, that the user is at risk of readmission to a medical facility comprises: based on determining that the detected increase exceeds the threshold level, detecting, by the one or more processing devices and based on analyzing, that the user is at risk of readmission to a medical facility comprises. The actions include waiting, for a predefined period of time, for information specifying that the member of the medical facility has performed the action; after the predefined period of time has elapsed, escalating the alert to one or more other members of the medical facility, wherein the alert is escalated by notifying the one or more other members of the medical facility. The actions include generating information for a graphical user interface that when rendered on a display device comprises: a first visual indicator of first answers of the user to a first question pertaining to a first one of the risk factors, with the first answers being displayed in the graphical user interface over a period of time; and a second visual indicator of second answers of the user to a second question pertaining to a second one of the risk factors, with the second answers being displayed in the graphical user interface over the period of time. The actions include exporting the generated information for the graphical user interface, with the information being exported to a client computing device associated with one or more of a government entity, a history, an electronic medical record entity, and a business intelligence entity. The graphical user interface further comprises: a visual indicator of the alert and an explanation of the reason for the alert. The risk of readmission is associated with a particular risk factor from the risk factors, wherein the information indicative of answers to the plurality of questions comprises first information, and wherein the method further comprising: receiving information specifying that the member of the medical facility has performed the action; following receipt of the information specifying that the member of the medical facility has performed the action, periodically receiving, from the client computing device, second information indicative of answers to questions regarding the particular risk factor; analyzing, by one or more processing devices and over a predefined period of time, the second information in comparison to the first information; determining, by the one or more processing devices and based on analyzing, that performance of that action has decreased the risk of readmission relative to the risk of readmission prior to performance of the action. The risk of readmission is associated with a particular risk factor from the risk factors, wherein the information indicative of answers to the plurality of questions comprises first information, and wherein the method further comprising: receiving information specifying that the member of the medical facility has performed the action; following receipt of the information specifying that the member of the medical facility has performed the action, periodically receiving, from the client computing device, second information indicative of answers to questions regarding the particular risk factor; analyzing, by one or more processing devices and over a predefined period of time, the second information in comparison to the first information; determining, by the one or more processing devices and based on analyzing, that the risk of readmission following performance of the action is unchanged; and generating, by the one or more processing devices, another action to be performed by a member of the medical facility, with performance of the other action reducing the risk of readmission relative to other risks of readmission that are independent of performance of the other action. The risk of readmission is associated with a particular risk factor from the risk factors, wherein the information indicative of answers to the plurality of questions comprises first information, and wherein the method further comprising: receiving information specifying that the member of the medical facility has performed the action; following receipt of the information specifying that the member of the medical facility has performed the action, periodically receiving, from the client computing device, second information indicative of answers to questions regarding the particular risk factor; analyzing, by one or more processing devices and over a predefined period of time, the second information in comparison to the first information; determining, by the one or more processing devices and based on analyzing, that the risk of readmission following performance of the action is above a threshold level; and generating, by the one or more processing devices, another action to be performed by a member of the medical facility, with performance of the other action reducing the risk of readmission relative to other risks of readmission that are independent of performance of the other action.

In still another aspect of the disclosure, the method includes transmitting, to a client computing device associated with a medical patient, information indicative of a risk factor questionnaire of a medical service provider, with the risk factor questionnaire comprising a plurality of questions regarding risk factors of the medical patient; periodically receiving, from the client computing device, information indicative of answers to the plurality of questions regarding the risk factors of the medical procedure; accessing, from a data repository, a medical alert rule, with the medical alert rule specifying one or more instructions for detecting a triggering event, with the triggering event specifying that the medical service provider has specified that a particular answer to a question is unacceptable and requires that the medical service provider be notified of the unacceptable answer; detecting, by one or more processing devices in the received information indicative of answers, the triggering event for at least one of the answers, with the triggering event specifying that the medical service provider has specified that the at least one of the answers to the question is unacceptable and requires that the medical service provider be notified of the unacceptable answer; determining, based on detection of the triggering event, that the user is at risk of readmission to a medical facility; generating, by the one or more processing devices, an action to be performed by a member of the medical facility, with performance of the action reducing the risk of readmission relative to other risks of readmission that are independent of performance of the action; and transmitting, to a client computing device associated with the medical facility, an alert of the generated action to promote the member of the medical facility to perform the action and to notify the member of the unacceptable answer. Other embodiments of this aspect include corresponding computer systems, apparatus, and computer programs recorded on one or more computer storage devices, each configured to perform the actions of the methods.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

BRIEF DESCRIPTION OF THE FIGURES

FIGS. 2-7 are screen images of graphical user interfaces generated by one or more applications (and/or a system) that can be used to interface with aspects of the system used by the medical service provider.

Like reference symbols in the various drawings indicate like elements.

DETAILED DESCRIPTION

Figure 1:
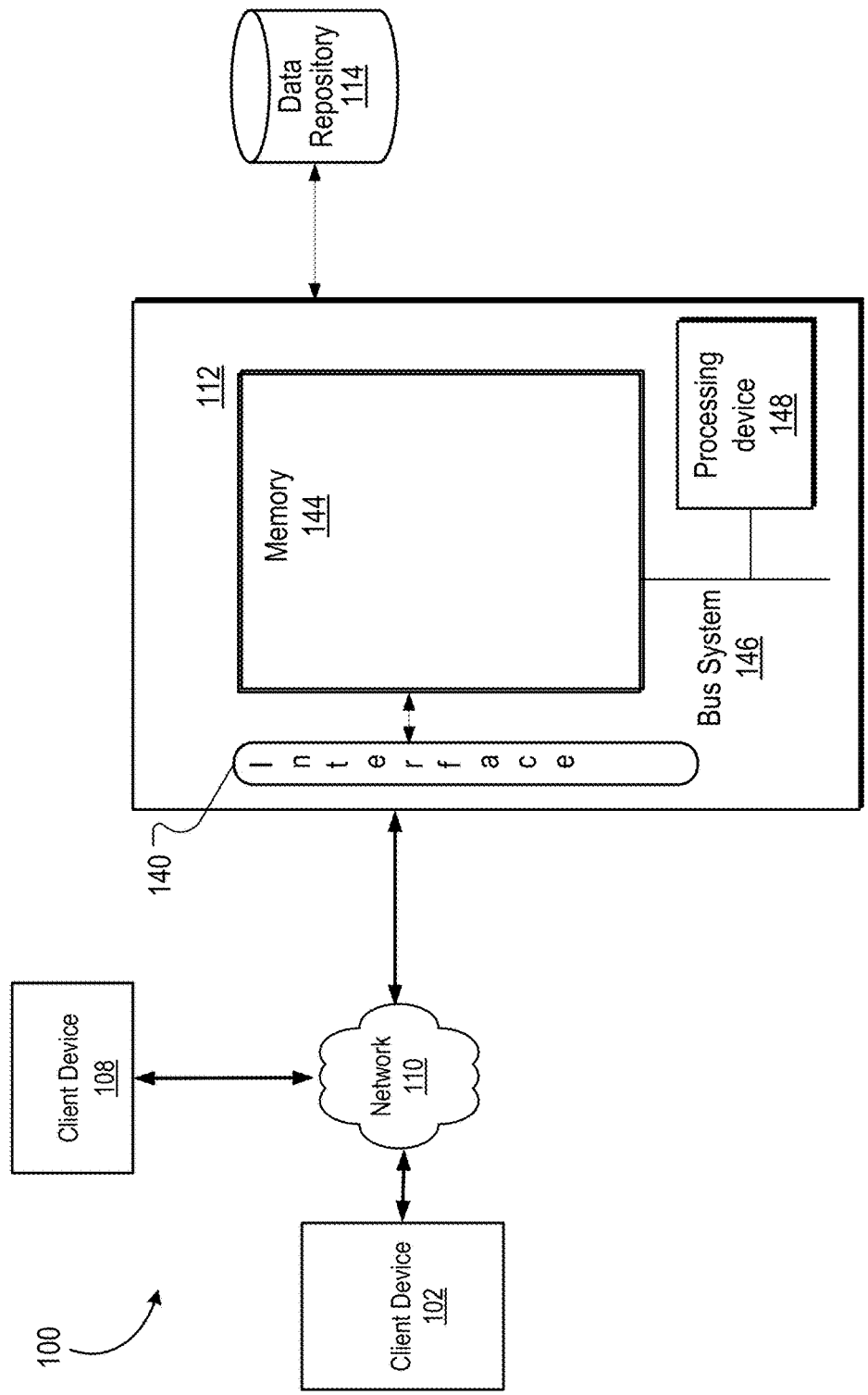
FIG. 1 is a block diagram of components of a system used by a medical service provider

In general, generating and processing medical questionnaire alerts by a medical service provider is described. The processing of these alerts results in re-admission reduction. In an example, the medical service provider can be some combination of a hospital, a clinic, other medical facility, one or more physicians, nurses, and other medical service professionals that provide medical care to one or more medical patients. In an example, a medical patient that has undergone a hip-replacement surgery can have a scheduled follow-up visit with the surgeon as part of the after-surgery recovery protocol. In an example, the follow-up visit is a routine visit, for example, periodically scheduled as part of the after-surgery recovery protocol. In another example, the follow-up visit may be in response to a particular occurrence of an event, such as a fever, fall, onset of pain, or for other reasons.

In general, when a patient visits the medical service provider, the patient can be presented with a medical assessment questionnaire (e.g., a risk assessment questionnaire). In an example, the medical assessment questionnaire can be provided electronically, e.g., on a handheld device or other mobile computing device. In general, the medical assessment questionnaire includes one or more questions and each question can be directed to a different aspect of the medical patient's care and having answers that are suitable to the information being sought. In an example, the questions included in the medical assessment questionnaire can be directed to the one or more reasons for the patient's visit. In a particular example, if the patient has undergone a hip-replacement surgery, the medical assessment questionnaire can include questions that are designed to obtain information that may be useful in identifying complications associated with the hip-replacement surgery. In some implementations, the medical service provider can compose the medical assessment questionnaire.

In general, each of the questions associated with the medical assessment questionnaire can be associated with acceptable answers and unacceptable answers. In a particular example, a question in the medical assessment questionnaire may be directed to an amount of pain the medical patient is currently experiencing. In this particular example, an acceptable answer may correspond to an answer that is below a predetermine threshold value while an unacceptable answer corresponds to an answer that is above the predetermined threshold value. In an example, if the predetermined threshold value for pain is five, an acceptable answer is four or less and an unacceptable answer is five or more.

When, for example, an unacceptable answer is received, a medical questionnaire alert can be automatically generated and stored that alerts the medical service provider that the medical patient has one or more medical symptoms that may need medical attention. In some implementations, the answers to particular questions on the medical assessment questionnaire can be tracked to determine when a particular answer is trending in an unacceptable direction. When, for example, an unacceptable trend is determined, even when a particular answer is still considered an acceptable answer (e.g., by not exceeding a threshold level), a medical questionnaire alert may be generated and stored to alert the medical service provider that medical intervention may be needed.

In general, a medical service provider can review a medical patient profile for one or more medical patients. When a medical questionnaire alert is generated and stored for a particular medical patient, the medical questionnaire alert can be displayed in the medical patient profile for the respective medical patient. As a result, the medical service provider can ascertain potential medical issues before meeting with the particular medical patient, providing more efficient patient visits.

In general, FIGS. 1-11 are described in relation to the collection and use of certain personal medical information of one or more users. The processes and procedures used by the medical service provider described herein for the collection and use of the personal medical information are compliant with the Health Insurance Portability and Accountability Act (HIPPA) and any other relevant regulations for the protection of personal medical information and other information. In addition, in some implementations, aspects of some or all of the information that is collected by the medical service provider can be anonymized to add additional privacy protections for the medical patients of the medical service provider.

FIG. 1 is a block diagram of components of a system 100 that can be operated by a medical service provider. Again, the medical service provider can be some combination of a hospital, a clinic, and one or more physicians, nurses, and other medical service professionals that provide medical care to one or more medical patients. In FIG. 1, client devices 102, 108 can be any sort of computing devices capable of taking input from a user and communicating over network 110 with server 112 and/or with other client devices. For example, client devices 102, 108 can be mobile devices, desktop computers, laptops, cell phones, personal digital assistants ("PDAs"), servers, embedded computing systems, and so forth. In a particular example, the client devices 102 and 108 are tablet computing devices or other computing devices that include a touch-sensitive input-and-display device that allows a medical patient using the client devices 102 and 108 to provide medical assessment answers by touching appropriate regions of a presented medical assessment questionnaire.

In an example, the client devices 102 and 108 are configured to present one or more graphical users interfaces to their respective users. In a particular example, the client devices 102 and 108 have been installed with an application or other executable code. The application or executable code can cause presentation of the graphical user interfaces when the application or executable code is executed, e.g., by a processing device 148. These graphical user interfaces allow users to enter information indicative of the user's medical recovery and allow the server 112 to assess whether the user is at risk for re-admission. Particular examples of graphical user interfaces are described in more detail below.

Server 112 can be any of a variety of computing devices capable of receiving data, such as a server, a distributed computing system, a desktop computer, a laptop, a cell phone, a rack-mounted server, and so forth. Server 112 may be a single server or a group of servers that are at a same location or at different locations.

In general, the server 112 can serve as platform for the system 100 whereby medical patients can provide one or more answers to questions and where the answers are used to generate one or more appropriate medical questionnaire alerts. In an example, each of the client devices 102 and 108 can communicate with the server 112 and provide data indicative of a answers to a medical assessment questionnaire to the server 112.

The illustrated server 112 can receive data from client devices 102, 108 via input/output ("I/O") interface 140. I/O interface 140 can be any type of interface capable of receiving data over a network, such as an Ethernet interface, a wireless networking interface, a fiber-optic networking interface, a modem, and so forth. Server 112 also includes a processing device 148 and memory 144. A bus system 146, including, for example, a data bus and a motherboard, can be used to establish and to control data communication between the components of server 112.

The illustrated processing device 148 may include one or more microprocessors. Generally, processing device 148 may include any appropriate processor and/or logic that is capable of receiving and storing data, and of communicating over a network (not shown). Memory 144 can include a hard drive and a random access memory storage device, such as a dynamic random access memory, or other types of non-transitory machine-readable storage devices. Memory 144 stores computer programs (not shown) that are executable by processing device 148 to perform the techniques described herein. In a particular example, the memory can store a rules engine that can detect a triggering event and cause a medical questionnaire alert to be generated.

In an example, server 112 generates and implements a medical questionnaire alert generator. In an example, the server 112 can receive medical assessment questionnaires composed by medical service providers. At some future time (e.g., when a medical patient visits the medical service provider), the server 112 can provide the medical assessment questionnaires to the client devices 102 and 108. As the medical patient completes the medical assessment questionnaire, the server 112 can receive medical assessment answers from the client devices 102 and 108. In response, the server 112 can generate one or more medical questionnaire alerts based at least in part on the medical assessment answers, store the alerts in the data repository 114, and generate a graphical alert for the medical service provider. Additional aspects of the server 112 are described elsewhere in this specification.

Referring now to FIGS. 2-8, server 112 can generate information for one or more graphical user interfaces that provide information to a user of the medical service provider. In general, this information can be indicative of various things to aid the medical service provider in making informed decisions with respect to the medical care of the respective medical patients under the care of the medical service provider. In an example, the information can be indicative of potential medical complications associated a medical procedure that a particular medical patient has undergone.

In general, at least some of the graphical user interfaces can be rendered by an application installed on a client device 102 or 108 (FIG. 1) as part of execution of the application. In an example, the graphical user interfaces can be rendered by an application that when executed generates the graphical user by loading graphical resources stored on the client device 102 or 108 and installed as part of the installation of the application. In another example, the graphical user interfaces can be generated by a browser-based application that generates that graphical user interfaces by receiving and interpreting information indicative of one or more web pages provided by the server 112.

Figure 2:
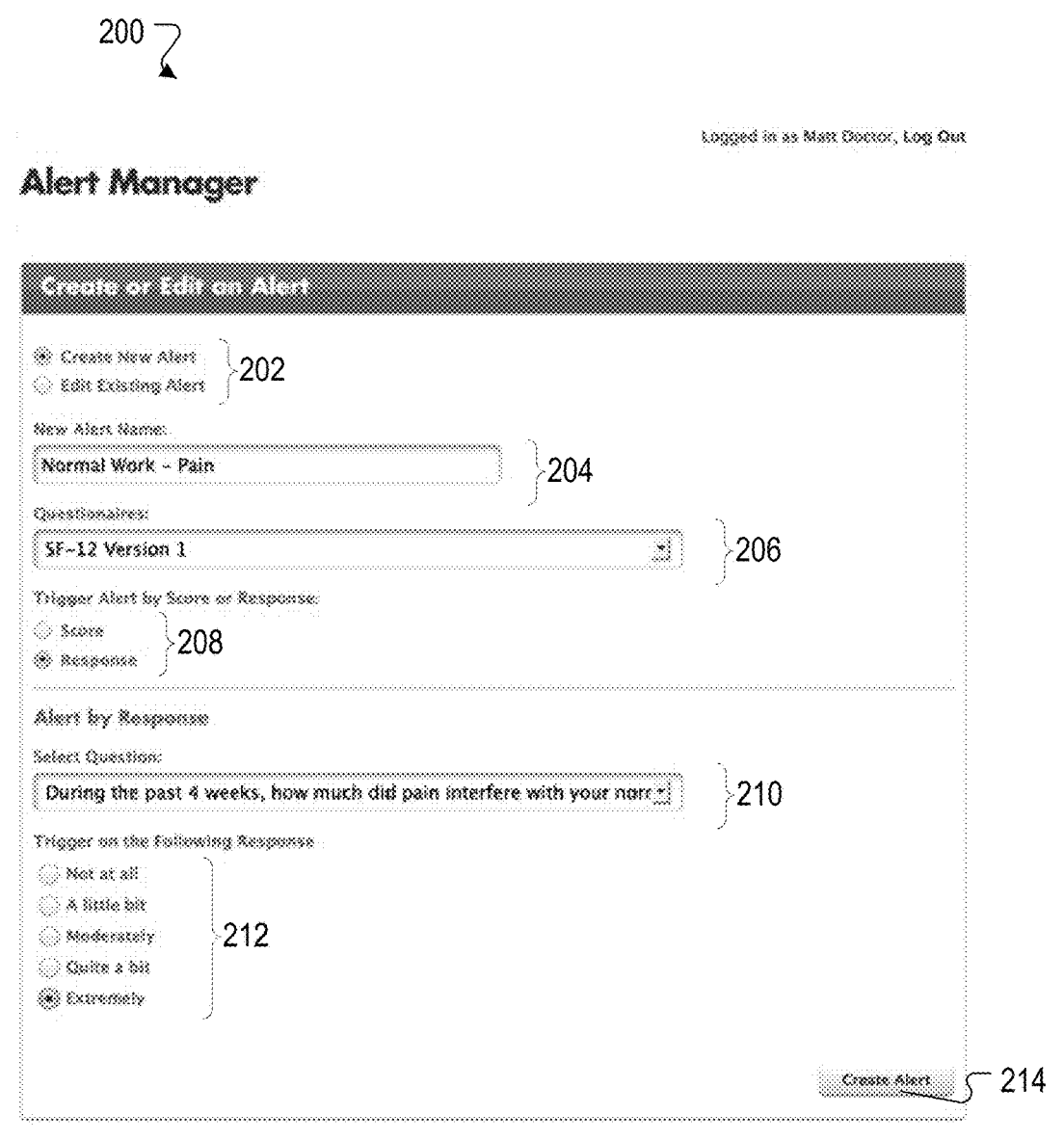

FIG. 2 is a screen image of an example graphical user interface 200 that can be used to generate or otherwise configure one or more medical questionnaire alerts. In general, a physician or other medical care professional can access or login to the server 112 (FIG. 1). In response, the sever 112 can provide the graphical user interface 200 on a computing device being operated by the medical care professional. In general, the graphical user interface 200 can include one or more regions or user interface components that can be used by the medical care professional to generate or otherwise configure the one or more medical questionnaire alerts. In a particular example, the graphical user interface 200 can include an alert region 202, a name region 204, a questionnaire selection region 206, a rule region 208, a question selection region 210, a trigger selection region 212, and a create alert user interface control 214.

The alert region 202 allows a user presented with the graphical user interface 200 to select from one or more medical questionnaire alert workflows. In a particular example, the alert region 202 allows a user to select a workflow to create a new medical questionnaire alert or a workflow to edit an existing alert. In the depicted example, the alert region 202 includes multiple radio box user input controls that allow a user being presented with the graphical user interface 200 to select a desired workflow. In this particular example, because the alert region 202 uses radio box user input controls, only one of the workflows that is associated with respective ones of the one or more radio box user input controls in the alert region 202 can be selected.

In the depicted example, the "Create New Alert" radio box user interface control has been selected. As a result, the "Edit Existing Alert" radio box user interface control is not selected. Depending on which user interface control and corresponding workflow is selected in the alert region 202, the graphical user interface 200 may change accordingly. Other types of user input controls (e.g., checkboxes and other user input controls) can also be included in the alert region 202. As a result, behavior of the graphical user interface may be different based on the user input controls included in the alert region 202. Examples of differences in the graphical user interface 200 based on which workflow is selected are described in more detail below.

The name region 204 allows a user that is presented with the graphical user interface 200 to provide or select a name for a particular medical questionnaire alert. In the depicted example, because the "Create New Alert" workflow is selected in the alert region 202, the name region 204 includes an edit box that enables the user to provide one or more characters indicative of a name of a new medical alert. When, for example, the "Edit Existing Alert" workflow is selected in the alert region 202, the name region 204 can include a drop down control or other user input control that enables a user to select a pre-existing medical questionnaire alert, such as a medical questionnaire alert that has been previously generated and stored using the "Create New Alert" workflow.

The questionnaire selection region 206 allows a user presented with the graphical user interface 200 to select a particular medical assessment questionnaire in which to associate a particular medical questionnaire alert. In the depicted example, because the "Create New Alert" workflow has been selected in the alert region 202, the questionnaire selection region 206 is a drop down user input control that enables the user to select one a previously generated medical assessment questionnaire in which to associate the new medical questionnaire alert. When, for example, the "Edit Existing Alert" workflow has been selected in the alert region 202, the questionnaire selection region 206 may prevent user interaction to indicate that the questionnaire region 202 is only providing the name of the questionnaire in which the existing medical questionnaire alert is associated. In some implementations, even when the "Edit Existing Alert" workflow has been selected, the questionnaire selection region 206 may still be a drop down user input control that enables the user to associate a previously generated and stored medical questionnaire alert with a different medical assessment questionnaire.

The rule region 208 enables a user presented with the graphical user interface 200 to select one or more triggering event for the particular medical questionnaire alert. In an example, the triggering event can be a combination of a score or a response. In a particular example, a score can be a predefined numerical range (e.g., the range zero to one-hundred, the range one to ten, and so forth), while a response can be a predetermined answer (e.g., "not at all" or "extremely").

In the depicted example, the rule region 208 includes multiple radio box user input controls that allow a user being presented with the graphical user interface 200 to select a desired triggering event. In this particular example, because the rule region 208 uses radio box user input controls, only one of the triggering events that is associated with respective ones of the one or more radio box user input controls in the rule region 208 can be selected. In the depicted example, the "Response" radio box user interface control has been selected. As a result, the "Score" radio box user interface control is not selected. Other types of user input controls (e.g., checkboxes and other user input controls) can also be included in the rule region 208. As a result, behavior of the graphical user interface may be different based on the user input controls included in the rule region 208. In some implementations, aspects of the graphical user interface 200 may change based on whether a score triggering event or a response triggering event is selected. Score triggering events, response triggering events, and differences in the graphical user interface 200 based on a selection of the type of triggering event are described in more detail below.

The question selection region 210 enables a user of presented with the graphical user interface 200 to select a particular question included in the medical assessment questionnaire. In the depicted example, the question selection region 210 includes drop down use interface component that enables the user to select one of medical assessment questions included in the medical assessment questionnaire. In some implementations, the question selection region 210 may include more or other user interface components. In an example, the question selection region 210 may include a list of available questions enabling the user to select multiple questions. In this particular example, a user may want to select multiple medical assessment questions to specify which of the medical assessment questions to consider when the score triggering event is selected. In other words, in some implementations, when a score triggering event is specified (e.g., using rule region 208), the user can specify the scores of the particular medical assessment questions to aggregate when comparing whether the aggregate score is sufficient to operate as a triggering event.

The trigger selection region 212 enables a user presented with the graphical user interface 200 to select one or more triggers that can be compared to one or more answers provided by a medical patient answering the selected medical assessment question. In an example, when a response triggering event is selected (e.g., using the rule region 208), the trigger selection region 212 represents specific answers to the selected medical assessment question. In another example, when a score triggering event is selected (e.g., using the rule region 208) an edit box or other user interface control can be provided that does not reflect a specific answer to a medical assessment question, but instead reflects a score associated with a specific answer or collection of answers. In this particular example, when a user answers a medical assessment question associated with their pain, the answer to that medical assessment question can be converted into a score and compared with the triggering event score or the determined score can be aggregated with scores of other answers to other medical assessment questions. The score (either an individual score or an aggregated score) can be compared with the triggering event score.

In the depicted example, because a response trigger has been selected in the rule region 208, the trigger selection region 212 includes multiple radio box user input controls that allow a user being presented with the graphical user interface 200 to select a desired triggering event. In this particular example, because the triggering selection region 212 uses radio box user input controls, only one of the triggering events that is associated with respective ones of the one or more radio box user input controls in the rule region 208 can be selected. In the depicted example, the "Extremely" radio box user interface control has been selected. As a result, others of the radio box user input controls "Not at all," "A little bit," "Moderately," and "Quite a bit" are not selected. Other types of user input controls (e.g., edit boxes, checkboxes and other user input controls) can also be included in the trigger selection region 212.

The create alert user interface potent enables a user presented with the graphical user interface 200 to generate and store a medical questionnaire alert based on the information that the user provided in the graphical user interface 200. In an example, when the user selects the button, a medical questionnaire alert is generated using the provided information. In a particular example, by selecting the create alert user interface control 214, a user can cause the server 112 (FIG. 1) to generate a medical questionnaire alert based on the information included in the graphical user interface 200 and store the medical questionnaire alert in the data repository 114 (FIG. 1) associated with a particular medical assessment questionnaire. After a medical questionnaire alert has been generated, medical patients can trigger the medical questionnaire alert based on answers that respective ones of the medical patients provide when they visit a medical service provider.

Figure 3:
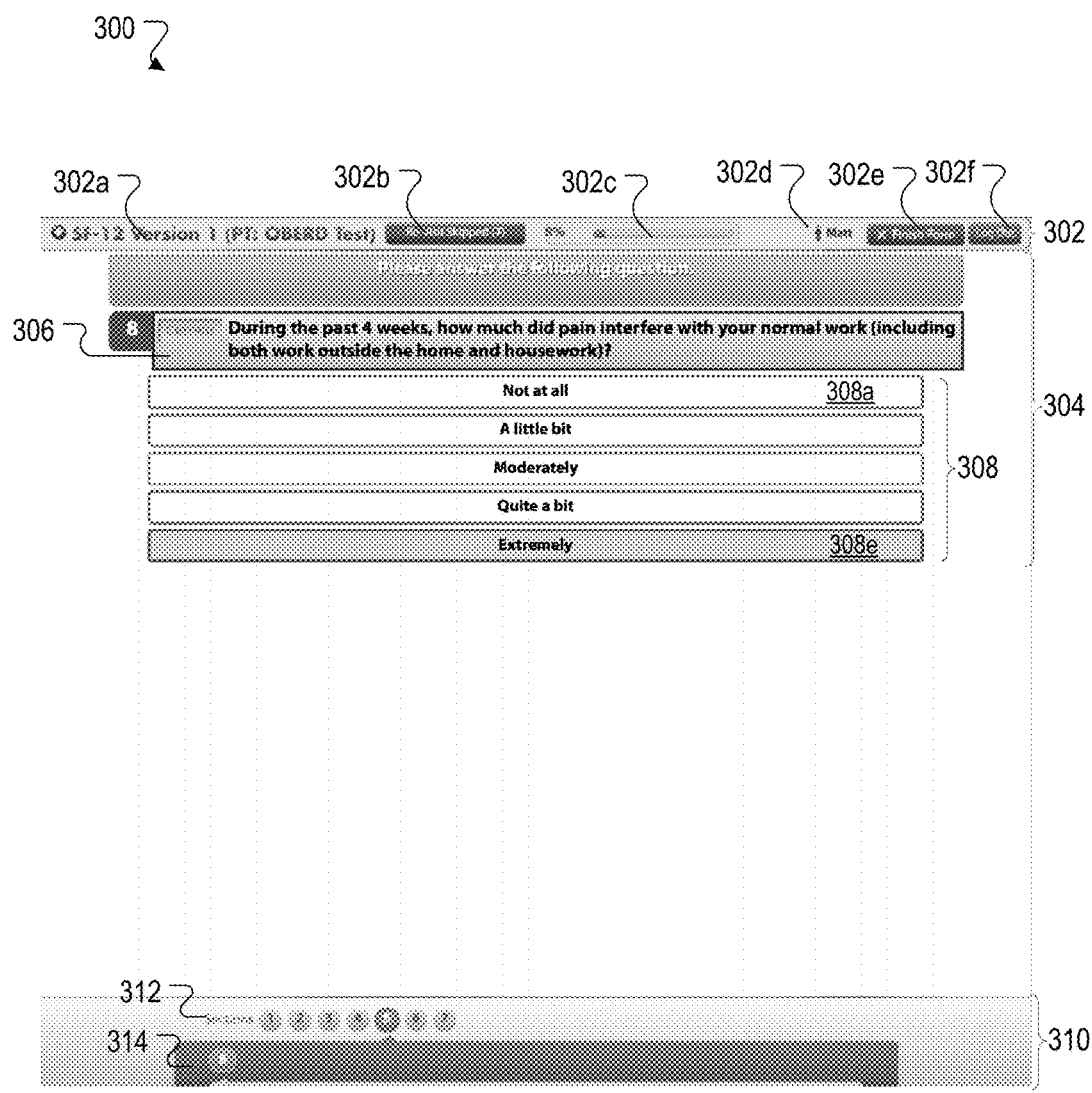

FIG. 3 is a screen image of graphical user interface 300 that can be used to present medical assessment questions included in a medical assessment questionnaire. The graphical user interface includes a number of regions that can be used to present information to a medical patient and receive input provided by the medical patient. In a particular example, the graphical user interface 300 includes a status region 302, an answer region 304, and a medical assessment questionnaire selection region 310 although other regions can also be presented.

The status region 302 includes a number user interface components or other display areas 302a-302f that presents various information to a medical patient answering a presented medical assessment questionnaire. In a particular example, display area 302a presents a name of the medical assessment questionnaire. In a particular example, user interface control 302b presents a number of skipped medical assessment questions and can be selected by the medical patient to revisit those skipped questions. In a particular example, display area 302c presents an amount of the medical assessment questionnaire that the medical patient has completed. In this particular, the amount is presented as a percentage, although the amount can be presented in other ways, including a number of medical assessment questions answered and a number of medical assessment questions remaining to be answered.

In a particular example, the display area 302d presents an identifier for the medical patient. In this particular example, a name of the medical patient is presented, although an identifier can be presented in other ways, including a patient identifier number, or other identifier. In a particular example, the user interface control 302e allows a medical patient to submit the medical assessment questionnaire. In the particular example, when the medical patient selects the use interface component 302e, the answers to the medical assessment questionnaire are provided to the server 112 (FIG. 1). In some implementations, the user interface control 302e may be excluded from the graphical user interface 300 and each time a medical patient provides an answer to a medical assessment question, the answer can be provided to the server 112. In a particular example, the user interface control 302f may enable a user (e.g., a medical patient or a medical professional associated with a medical service provider) to log the medical patient out of the medical assessment questionnaire. In some implementations, when a medical patient is logged out of the medical assessment questionnaire, the answers to the medical assessment questions are provided to the server 112 and an application presenting the medical assessment questionnaire logs the medical patient out. This can effectively protect a first medical patient from another medical patient accidentally answering medical assessment questions on behalf of the first medical patient.

The answer region 304 enables the medical patient to read a medical assessment question and to provide an answer that corresponds to the medical patient's own assessment of his/her condition. In a particular example, the answer region 304 includes a question 306 and one or more responses 308. In this particular example, the responses 308 are color-coded to reflect an acceptability of the particular answers. For example, the response "Not at all" 308a has a green boundary to reflect or otherwise indicate a most acceptable answer to the question 306 "During the past 4 weeks, how much did pain interfere with your normal work (including both work outside the home and housework)?" and the response "Extremely" 308e has a red boundary to reflect a most unacceptable answer to the same question.

In some implementations, once a response has been selected, the particular response can be filled with a color that corresponds to the boundary color of the particular response. In a particular example, because the response "Extremely" 308e has been selected by the medical patient as an assessment of the medical patient's condition, the response "Extremely" 308e is filled with a red color. Contrasted with, for example, the response "Not at all" 308a, a medical patient can make sure that the response 308 that they believe is selected will be the response provided to the server 112 (FIG. 1) when the medical assessment questionnaire is provided to the server 112.

The medical assessment questionnaire selection region 310 enables the medical patient to select a combination of a section of the medical assessment questionnaire or a particular medical assessment question for which to provide answers. As a result, the medical assessment questionnaire selection region 310 enables the medical patient to quickly navigate between sections of the medical assessment questionnaire and to quickly select particular questions include in a selected section. In a particular example, the medical assessment questionnaire selection region 310 includes a collection of user interface components 312 that correspond to a number of sections included in the medical assessment questionnaire. In this particular example, the medical patient has selected a section that corresponds to section "5" of the medical assessment questionnaire. As a result, the medical assessment questionnaire selection region 310 can also present one or more user interface components 314 for questions that are associated with the selected section. In this particular example, only one question, question "8" is associated with the selected section, and so only one user interface control 314 is presented.

Figure 4:
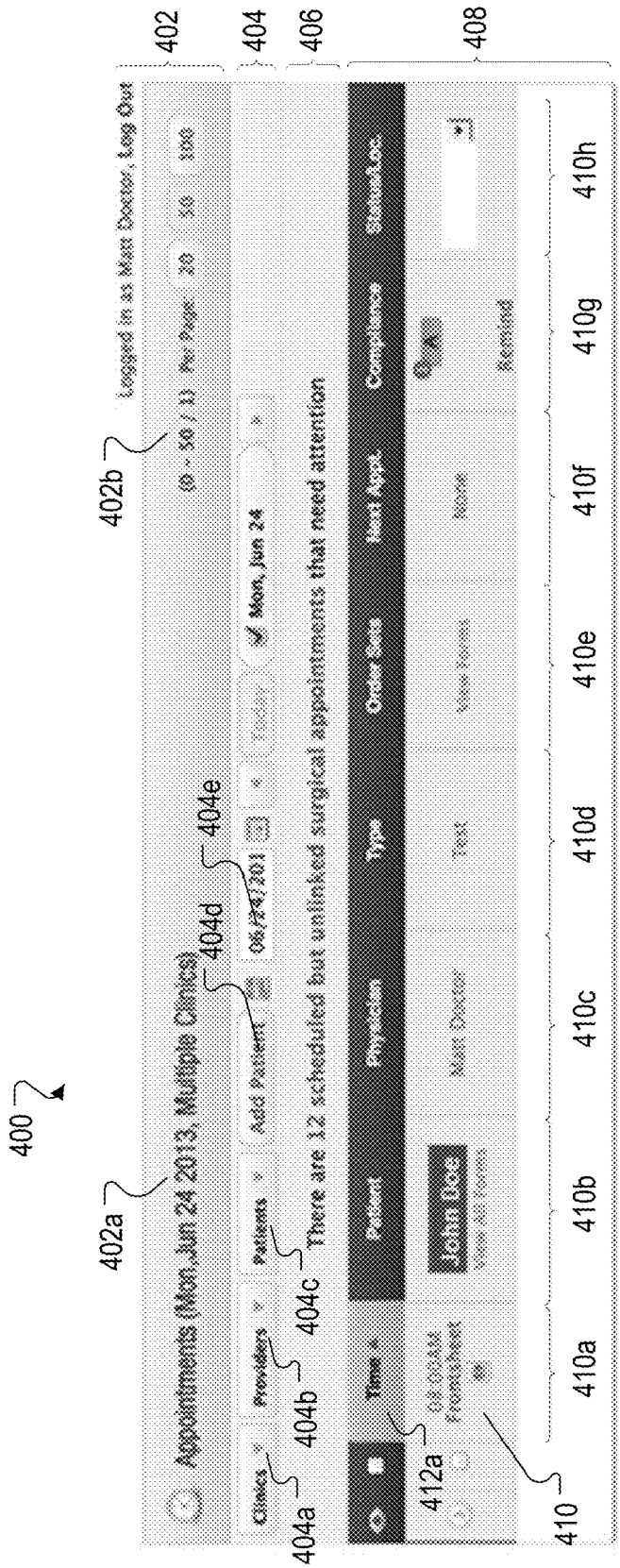

FIG. 4 is a screen image of a graphical user interface 400 that can be used by a medical professional to view and manage medical appointments. The graphical user interface can include various regions including a status region 402, a search region 404, a message region 406, and a results region 408.

In an example, the status region 402 includes a text region 402a and a selection region 402b that allows a user presented with the graphical user interface 400 to select a number of search results to provide in the results region 408. In a particular example, the text region 402a shows the date range of the appointments to be searched and which clinics, hospitals, or other locations are included in the search. In a particular example, the selection region 402b includes one or more user interface components that enable the user to select between twenty search results, fifty search results, and one-hundred search results to be shown per page in the results region 408.

The search region 404 presents one or more user interface components that allow a user presented with the graphical user interface to search for particular appointments based on one or more characteristics associated with the appointment. In a particular example, the search region provides user interface components that enable the user to search for appointments using a clinic user interface control 404a (e.g., for searching by clinic), a provider user interface control 404b (e.g., for searching by provider), a patient user interface control 404c (e.g. for searching by patient), and a date picker user interface control 404e (e.g., for searching by date).

In an example, the clinics user interface control 404a is a drop down user interface control that enables the user to select one of the clinics, hospitals, or other locations in which a particular medical professional is affiliated. In an example, the insurance provider user interface control 404b is a drop down user interface control that enables the user to select an insurance provider that the medical service provider accepts and that is used by one or more medical patients that are seen by the medical service professional. In an example, the patient user interface control 404c is a drop down user interface control that enables the user to select a particular medical patient that frequents the medical service provider. If, for example, a particular patient does not appear in the drop down list, the user can select the add patient user interface control 404d to add the patient to the system and by extension to the patient user interface control 404c. In an example, the date picker user interface control 404e can be a calendar or other user interface control that enables the user to select a particular date in which to search for appointments.

In an example, a notification region 406 can provide various notifications to a user that correspond with information associated with the various appointments maintained by a system, such as server 112 (FIG. 1). In general, the notification region 406 includes notifications that require some form of user intervention. In a particular example, the notification region 406 includes a notification that scheduled appointments are not linked to medical patients and that an action is required. In this example, the action may be for an administrator or other member of the medical service provider to access appointment information and to link unlinked appointments with particular medical patients, although other messages and actions can be presented and processed by a system presenting the graphical user interface 400. In some implementations, when the notifications are not handled in a timely manner, the notifications can be escalated to other individuals associated with the medical service provider. In an example, when an administrator does not address a notification in a timely fashion, the notification can be escalated to the administrator's supervisor.

In an example, when a user selects one or more of the user interface components in the search region 404, a system, such as server 112 (FIG. 1) can access a data repository, such as data repository 114 (FIG. 1) to identify one or more appointments that match the search criteria provided in the search region 404. As a result, the results region 408 can be populated using information stored in the data repository 114 that is responsive to the search criteria in the search region 404.

In general, the results region 408 can be a table 410 or other formatted data region that can include a number of different columns that can be used to provide different information about a particular medial patient that corresponds to a row of the table in the search region 408. In a particular example, the table 410 included in the results region 408 can include a time column 410a, a patient column 410b, a physician column 410c, a type of procedure column 410d, an order sets column 410e, a next appointment column 410f, a compliance column 410g, and a status and location column 410h.

In an example, the time column 410a can present information indicative of a time of an appointment for the particular patient. In an example, the patient column 410b can present information indicative of the particular patient. In a particular example, the patient column 410b may include a user interface control that allows a medical service professional viewing the graphical user interface 400 to view a patient profile or other information associated with the patient. An example patient profile is described in reference to FIG. 5.

In an example, the physician column 410c can present information indicative of a physician or other medical service professional that is scheduled to meet with the medical patient. In an example, the type of procedure column 410d can present information indicative of a type of procedure (e.g., blood test, follow-up examination, or other procedure) that is associated with the particular appointment. In an example, the order sets column 410e provides information indicative of one or more order forms associated with procedure, test, or other action to be performed during the appointment. In some implementations, the order sets column 410e can present a user selectable link that allows a medical professional to order medical tests, x-rays, and other medically prescribed procedures either before or after the medical patient's appointment.

In an example, the next appointment column 410f presents information indicative of next appointment. For example, physical therapy may be scheduled on a recurring or other predetermined basis. Any next appointments can be shown in the next appointment column 410f. In some implementations, the next appointment column 410f can include a user selectable link that allows a medical profession to schedule or otherwise generate a next appointment for the particular medical patient.

In an example, the compliance column 410g provides information indicative of one or more medical alerts or other medical actions that have been generated, escalated, or are otherwise noteworthy. In the depicted example, the compliance column 410g shows a medical questionnaire alert that has been escalated, e.g., because an assigned medical professional was tardy in performing a prescribed action in response to receiving the medical questionnaire alert.

In an example, the status and location column 410h can provide information indicative of the status of medical patient and/or a location at which an appointment is to occur or a medical procedure is to be performed. In a particular example, the status and location column 410h includes a drop down user interface control that enables a medical professional to select a predefined status, location, or both to associate with the particular appointment.

In an example, headings associated with each of these columns can be selected which causes the table 410 to sort the information according to the selected column. In the depicted example, the "Time" heading 412a of the time column 410a has been selected by a user causing the results region to sort the information in the table 410 according to a chronological ordering of the appointments on Monday, June twenty-fourth (e.g., as indicated by the search region 404).

Figure 5:
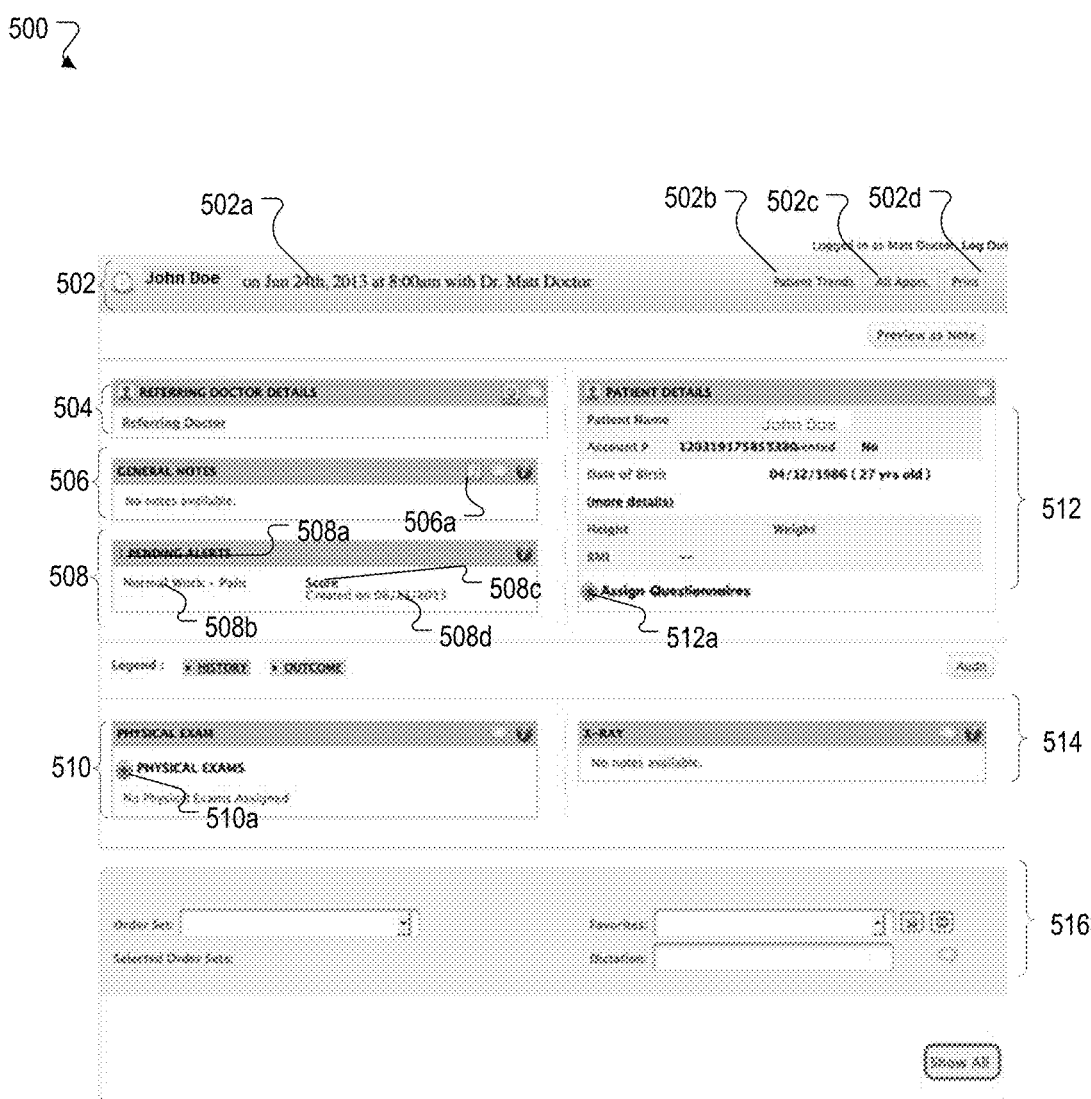

FIG. 5 is a screen image of a graphical user interface 500 that can be used to show information about a particular patient. In some implementations, the graphical user interface 500 can be presented to a medical professional in response to the medical professional selecting a user interface control in column 410b of the graphical user interface 400 (FIG. 4). In some implementations, the graphical user interface 500 can be presented in response to an application that presents graphical user interface 500 receiving other user input or for other reasons.

The graphical user interface 500 may include a number of regions that can present different information to a medical professional and enable the medical profession to perform certain actions. In an example, the graphical user interface 500 includes a status region 502, a referring doctor region 504, a general notes region 506, a pending alerts region 508, a physical exam region 510, a patient details region 512, an x-ray region 514, and a miscellaneous region 516.

In an example, the status region 502 provides a general status of the particular patient. In the depicted example, the status region 502 includes a text region 502a that presents information indicative of the particular patient, the time of the appointment, and the physician or other medical professional with which the medical patient is meeting. In an example, the status region 502 also includes a user interface control 502b that enables the medical professional to view information indicative of one or more trends regarding the progress of the medical patient. An example of information indicative of one or more trends is described in reference to FIG. 7, below. In an example, the status region 502 also includes user interface control 502c that enables the medical profession to view all appointments for this particular patient. In an example, the status region 502 also includes a user interface control that enables to medical professional to send the graphical user interface to a printer or other output device for printing.

In an example, the referring doctor region 504 includes information indicative of a referring physician or other medical professional. In a particular example, the referring doctor region 504 can include a selectable link that, when selected, presents information indicative of the referring physician or other medical professional in a browser or other application.

In an example, the general notes region 506 includes information indicative of notes that pertain to the medical patient. In some implementations, the information can be stored in a data repository, such as data repository 114 (FIG. 1). In some implementations, the general notes region 506 can include a user interface control 506a that, when selected, causes another graphical user interface or other input control to be displayed so that the medical professional can provide one or more notes that are stored in the data repository 114.

In an example, the pending alerts region 508 includes information indicative of one or more pending medical questionnaire alerts. In a particular example, the pending alerts region 508 includes a text region 508a that presents information indicative of a number of pending medical questionnaire alerts. In a particular example, the pending alerts region 508 also includes a text region 508b that presents information indicative of a medical assessment question that caused the medical questionnaire alert based on an answer provided by the medical patient. In a particular example, the pending alerts region 508 includes a text region 508c that presents information indicative of a type of triggering event (e.g., "Score" or "Response" as specified using graphical user interface 200 (FIG. 2)) that caused the medical questionnaire alert to be generated. In a particular example, the pending alerts region 508 also includes text region 508d that presents information indicative of when the medical questionnaire alert was generated.

In an example, the physical exam region 510 includes information indicative of one or more physical examinations performed by one or more medical professional on the medical patient. In a particular example, the physical exam region 510 includes a user interface control 510a that, when selected, enables the medical professional to order or otherwise prescribe a physical examination to be performed on the medical patient.

In an example, the patient details region 512 includes information indicative of characteristics of the medical patient, such as height, weight, date of birth, account number, and so forth. In a particular example, the patient details region 512 includes a user interface control 512a that, when selected, enables a medical professional to assign a particular medical assessment questionnaire to the medical patient. In general, the assigned medical assessment questionnaire can be stored in a data repository, such as data repository 114 (FIG. 1). As a result, on the medical patient's next visit, the assigned questionnaire can be identified in the data repository 114 and a corresponding medical assessment questionnaire administered to the medical patient before his/her visit with the medical professional.

In an example, the x-ray region 514 includes information indicative of one more x-rays of the medical patient. In some implementations, the x-ray region 514 includes a user selectable link that enables the medical professional to order one or more x-rays.

The miscellaneous region 516 includes one or more user interface components that enable the medical professional to manage the patient profile and to provide additional medical information. In a particular example, the miscellaneous region 516 enables a medical profession to select one or more order sets, upload or otherwise provide dictation information, and to perform other operations.

Figure 6:
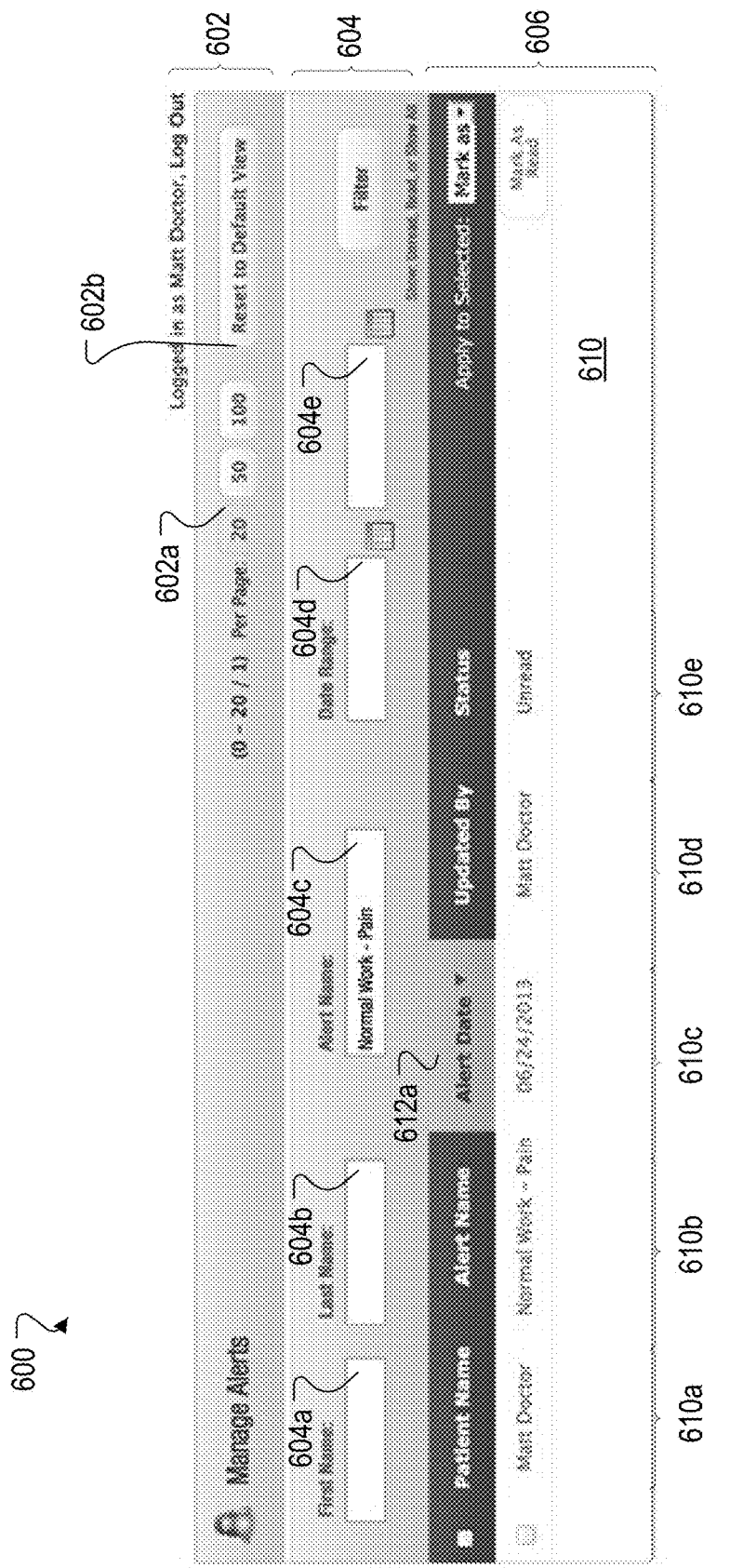

FIG. 6 is a screen image of a graphical user interface 600 that can present information indicative of one or more medical questionnaire alerts associated with one or more medical patients. The graphical user interface 600 can include various regions including a status region 602, a search region 604, and a results region 606.

In an example, the status region 602 includes a selection region 602a that allows a user presented with the graphical user interface 600 to select a number of search results to provide in the results region 606. In a particular example, the selection region 602a includes one or more user interface components that enable the user to select between twenty search results, fifty search results, and one-hundred search results to be shown per page in the results region 606. In an example, the status region 602 also includes a user interface control 602b that enables a user presented with the graphical user interface 600 to resets the search region 604 and the results region 606 to a default (e.g., empty or otherwise unselected) view.

The search region 604 presents one or more user interface components that allow a user presented with the graphical user interface to search for particular medial questionnaire alerts based on one or more characteristics associated with the alert. In a particular example, the search region 604 provides user interface components that enable the medical professional to search for alerts using a first-name user interface control 604a, a last-name user interface control 604b, an alert-name user interface control 604c, and a collection of date-range user interface components 604d and 604e, respectively.

In an example, the first-name user interface control 604a is an edit box that allows a medical profession to search for medical questionnaire alerts based on the first name of the medical patient. In an example, the last-name user interface control 604b is an edit box that allows a medical profession to search for medical questionnaire alerts based on the last name of the medical patient. In an example, the alert-name user interface control 604c is an edit box that allows a medical profession to search for medical questionnaire alerts based on the name associated with medical alert. In an example, the date-range user interface control 604d enables a medical professional to select a start date in which to conduct a search for the medical questionnaire alerts. In an example, the date-range user interface control 604e enables a medical professional to select an end date in which to conduct a search for the medical questionnaire alerts.

In an example, when a user selects one or more of the user interface components in the search region 604, a system, such as server 112 (FIG. 1) can access a data repository, such as data repository 114 (FIG. 1) to identify one or more appointments that match the search criteria provided in the search region 604. As a result, the results region 606 can be populated using information stored in the data repository 114 that is responsive to the search criteria in the search region 604.

In general, the results region 606 can be a table 610 or other formatted data region that can include a number of different columns that can be used to provide different information about a particular medical questionnaire alert that corresponds to a row of the table 610 in the search region 608. In a particular example, the table 610 included in the results region 606 can include a patient-name column 610a, an alert-name column 610b, a date column 610c, an update column 410d, and status column 610e.

In an example, the patient-name column 610a can present information indicative of a name of the medical patient to which particular medical questionnaire alert pertains. In an example, the alert-name column 410b can present information indicative of the name of a particular medical alert questionnaire. In a particular example, the alert-name column 610b can present names as defined by a user of the graphical user interface 200 (FIG. 2), and in particular, based on information entered into the name region 204.

In an example, the alert-date column 610c can present information indicative of when a particular medical questionnaire alert was generated. In an example, the update column 610d can present information indicative of a medical professional that has updated a status of the medical questionnaire alert. In an example, the status column 610e provides information indicative of status associated with the medical questionnaire alert, including whether the alert has been read, handled, escalated, and so forth according to one or more actions performed by various medical professionals.

In an example, headings associated with each of the columns 610a-610e can be selected which causes the table 610 to sort the information according to the selected column. In the depicted example, the "Alert Date" heading 612a of the alert-date column 610c has been selected by a user causing the results region 606 to sort the information in the table 610 according to a chronological ordering of when the medical questionnaire alerts presented in the table were generated.

In some implementations, any or all of the information presented in the various columns 610a-610e can be user-selectable allow a user presented with the graphical user interface 600 to view additional information associated with the selected information. In an example, if a user selects a status presented in the status column 610e, another graphical user interface may be presented that enables the user to review a status history of the one or more medical questionnaire alerts or to perform one or more actions associated with the medical questionnaire alert, or some combination of these.

Figure 7:
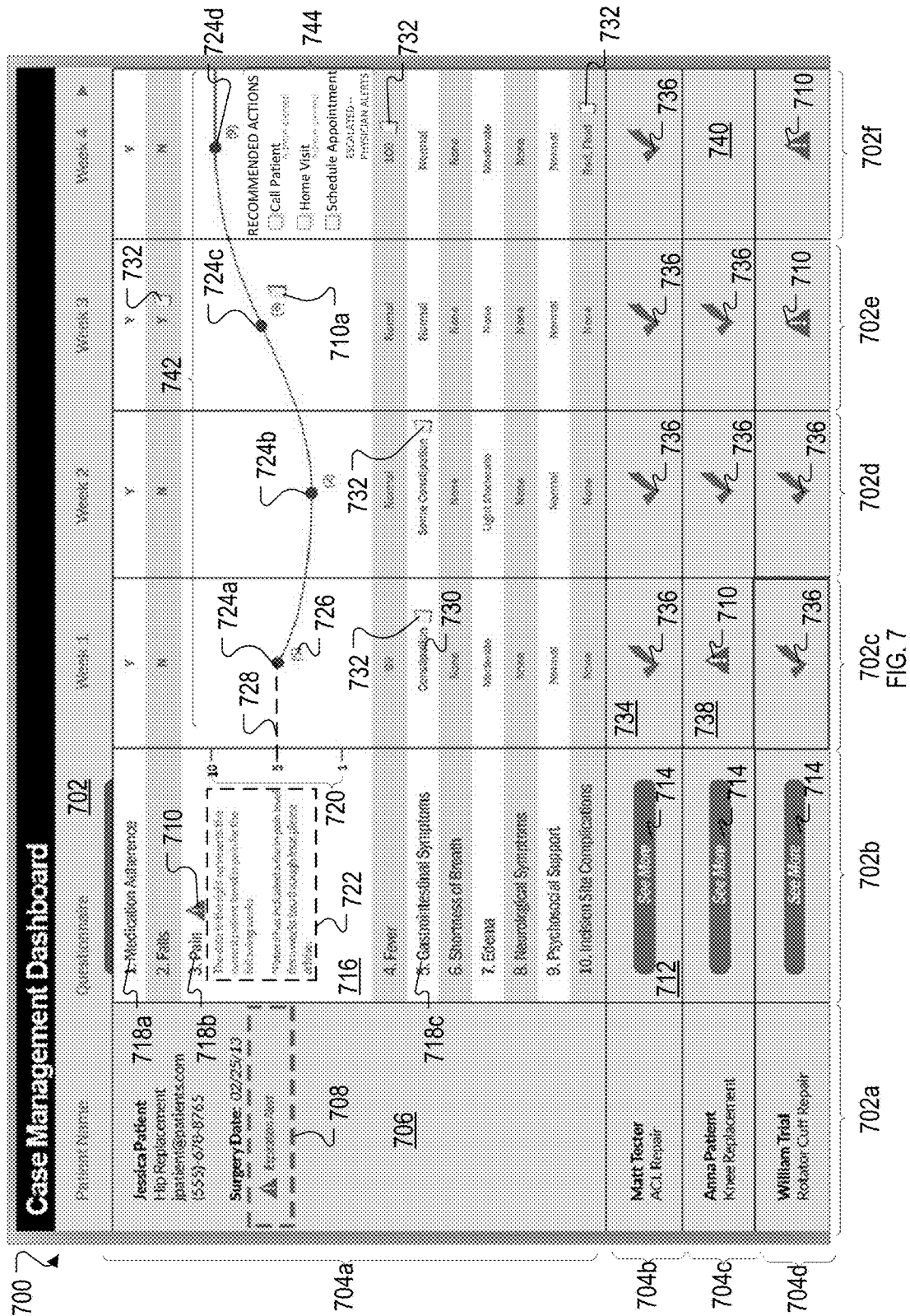

FIG. 7 is a screen image of a graphical user interface 700 that can be used to manage one or more medical questionnaire alerts for one or more patients. In general, the graphical user interface 700 can access information stored in a data repository 114 (FIG. 1) or other repository to present someone associated with a medical service provider a graphical representation of one or more medical patients as it pertains to one medical questionnaire alerts. In a particular example, the graphical user interface 700 can include table 702 or other representation of the information stored in the data repository 114. In an example, the table 702 can include a number of rows 704a-704d that present information for one or more medical patients, and one or more columns 702a-702f that present information about various aspects of the one or more medical patients and information associated with their recovery, e.g., as captured by answers to one or more medical assessment questionnaires.

In an example, column 702a can present information about a particular medical patient. In a particular example, column 702a of row 704a shows a data region 706 that presents the medical patient's name, procedure, contact information, date of procedure, and whether or not the medical patent has an associated medical questionnaire alert. In a particular example, a graphical icon 708 can be used to indicate medical questionnaire alert is present for the particular medical patient. In some implementations, a similar graphical icon 710 can be used to represent which portion of the table 702 includes a medical questionnaire alert. Examples of when the graphical icon 710 is described in more detail below.

Columns 702b-702f are now described. In general, the columns 702b-702f present information indicative of questions, answers, and medical questionnaire alerts that are associated with one or more medical assessment questionnaires. In an example, some or all of the data regions in the columns 702b-702f can include graphical interface components that enable a user viewing the user interface expand a particular data region or a particular row. In a particular example, data region 712 includes a graphical user interface control 714 labeled "See More" that can be used to expand the row 704b so data region 712 looks substantially similar to data region 716 in row 704a.

In an example, column 702b can present information indicative of one or more questions in a medical assessment questionnaire. In an example, a data region 716 can include particular questions. In some implementations, the particular questions can be selected by a user to expand the selected question to view a scale or other scoring mechanism for the particular question (e.g., as defined using graphical user interface 200). In a particular example, a question may first appear like question 718a and when a user selects a question, such as question 718b, an application presenting the graphical user interface 700 may cause the question to expand, showing a scale 720 from 1-10 that is indicative of a range of possible answers for the particular question 718b. In this particular example, an optional text region 722 may also be presented that describes the medical alert for the question 718b (e.g., as indicated by graphical icon 710 that is associated with question 718b).

In some implementations, some or all of the columns 702b-702f may include one or more graphical icon 736 that are indicative of some combination of one or more acceptable answers being provided the medical patient for a particular medical assessment questionnaire or that one or more actions associated with a medical questionnaire alert have been handled. As an example, if a medical questionnaire alert indicates that a particular medical patient should be contacted and that contact has occurred, graphical icon 736 can be displayed in particular data regions (e.g., data region 734) of the table 702. Alternatively, as an example, if a medical questionnaire alert indicates that a particular medical patient should be contacted and that contact has not occurred, graphical icon 710 may instead be displayed in particular data region (e.g., data region 738) of the table 702.

In some implementations, a data region (e.g., data region 740) may not include a graphical icon 710 or a graphical icon 736. In general, this may indicate that the particular medical patient has not completed or otherwise submitted a medical assessment questionnaire that was (or should have been) given to the medical patient on a particular visit. In a particular example, the medical patient identified in column 702*a* of row 704*c* has not provided answers to a medical assessment questionnaire provided on a fourth weekly-visit to a medical service provider (and/or to a medical facility). As a result, data region 740 is empty, indicating that particular medical patient does not answers for this visit.

In an example, column 702*c* can present information indicative of one or more answers provided by the medical patient to a medical assessment questionnaire given to the medical patient during a first visit to the medical service provider. In a particular example, column 702*c* shows a data point 724*a* that corresponds to an answer for a question that was provided by the medical patient as part of the medical patient completing a medical assessment questionnaire during a first visit to the medical service provider.

In some implementations, the placement of the data point 724*a* is based on the scale 720 or some other guide associated with a particular question. In a particular example, the data point 724*a* is positioned in the graphical user interface 700 according to relative position and placement of the scale 720. That is, an invisible line (illustrated by dashed line 728) can be drawn from the "5" in the scale 720 to the data point 724*a*. In some implementations, answers to questions are color-coded to indicate whether the answer to the question is an acceptable answer or an unacceptable answer. In a particular example, data point 724*a* is associated with text 726 that is color-coded green to indicate that the value (e.g., "5") is an acceptable answer. As another particular example, text 730 presenting an answer provided for question 718*c* is color-coded red to indicate an unacceptable answer.

In some implementations, one or more text regions can be associated with a graphical icon 732 that, when selected, allows a user of the graphical user interface to perform one or more tasks associated with the answer. In a particular example, a medical professional associated with the medical service provider can review the answer, provide notes associated with the answer (e.g., to schedule a follow-up appointment, document particular diagnosis associated with the answer, document findings associated with a medical test performed in response to receiving the an unacceptable answer, and so forth).

In an example, column 702*d* can present information indicative of one or more answers provided by the medical patient to a medical assessment questionnaire given to the medical patient during a second visit to the medical service provider. In a particular example, column 702*d* shows a data point 724*b* that corresponds to an answer for a question that was provided by the medical patient as part of the medical patient completing a medical assessment questionnaire during a second visit to the medical service provider.

In an example, column 702*e* can present information indicative of one or more answers provided by the medical patient to a medical assessment questionnaire given to the medical patient during a third visit to the medical service provider. In a particular example, column 702*e* shows a data point 724*c* that corresponds to an answer for a question that was provided by the medical patient as part of the medical patient completing a medical assessment questionnaire during a third visit to the medical service provider.

In an example, column 702*f* can present information indicative of one or more answers provided by the medical patient to a medical assessment questionnaire given to the medical patient during a fourth visit to the medical service provider. In a particular example, column 702*f* shows a data point 724*d* that corresponds to an answer for a question that was provided by the medical patient as part of the medical patient completing a medical assessment questionnaire during a fourth visit to the medical service provider.

In some implementations, each of the respective data points 724*a*-724*d* can also form a trend indicative of a medical condition or be otherwise used to generate a medical questionnaire alert. In a particular example, the data points 725*a*-724*d* can be used to generate a plot 742 that can graphically present a trend associated with the each of the data points 724*a*-724*d*. In some implementations, medical questionnaire alerts can be generated based on a formation of an unacceptable trend, even when the individual answers may be considered acceptable, if analyzed independently. In an example, an answer that corresponds to data point 724*c* may be considered an acceptable answer. Because there is a large jump from an answer that corresponds to data point 724*b* to an answer that corresponds to data point 724*c*, however, a medical questionnaire alert may still be generated.

In some implementations, the medical questionnaire alerts can be associated with one or more actions that are to be taken by the medical service provider as a mechanism for addressing possible medical complications associated with a medical alert. In an example, when medical pain exceeds a predetermined threshold, the medical service provider may call the patient, schedule a home visit, schedule an in-patient visit, or some combination. In some implementations, when at least one of the one or more actions are not performed in a timely manner, the actions may be escalated to another person associated with the medical service provider.

In an example, the graphical user interface 700 includes a recommended actions region 744 that includes a number of different actions that should be performed by someone associated with the medical service provider. In this example, the recommended actions region 744 includes a number of actions "Call Patient," "Home Visit," and "Schedule Appointment." In addition, actions presented in the recommended actions region 744 can be color-coded to reflect a seriousness or other priority that is associated with the particular action. In a particular example, the color-coding can be specified according to which person associated with the medical service provider the action is escalated. In an example, the "Call Patient" action is associated with yellow-color-coded text "Admin alerted" to reflect a combination of a medium priority and/or that a lack of action was escalated to an administrator associated with the medical service provider. In another example, the "Schedule Appointment" action is associated with red-color-coded text "Escalated—Physician Alerts" to reflect a combination of a high priority and/or that a lack of action was escalated to a physician associated with the medical service provider.

Figure 8:
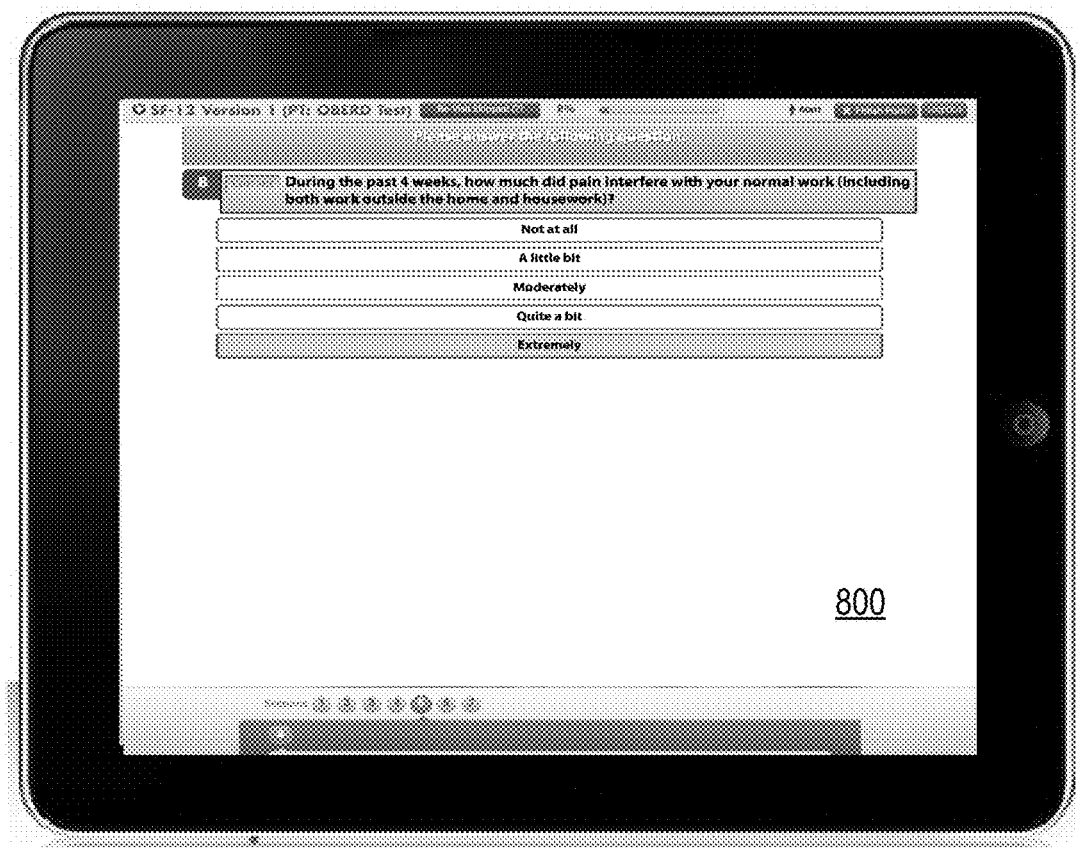
FIG. 8 shows a hand held device executing an application that generates the graphical user interfaces that can be used to interface with aspects of the system used by the medical service provider.

Referring now to FIG. 8, a screen image of a graphical user interface 800 is being shown as part of an application loaded on a client device 102 or 108, such as a tablet device 810. In the depicted example, the graphical user interface 800 is similar to the graphical user interface 300 (FIG. 3) that provides one or more medical assessment questions in the form of a medical assessment questionnaire. The graphical user interface 800, however, may be customized to fit a smaller screen of the handheld device 810 relative to other client device 102 or 108, such as a desktop computer, laptop computer, and so forth.

Figure 9:
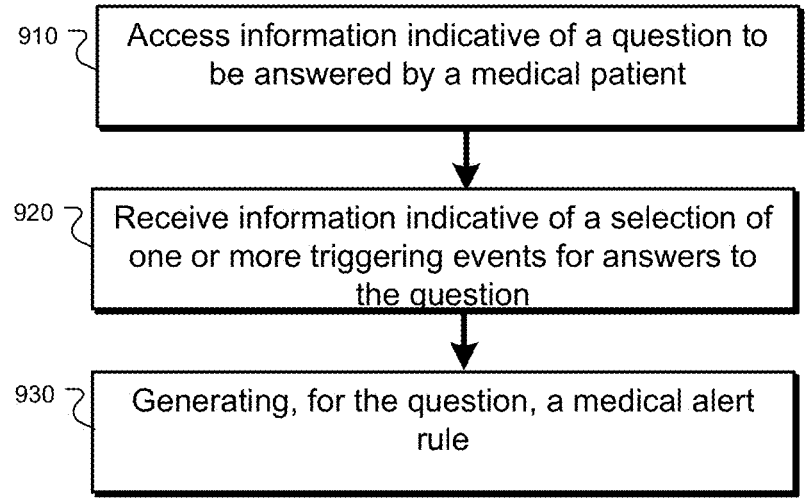
FIG. 9 is a flow chart of an example process that can be used to generate a medical alert rule.

FIG. 9 is a flow chart of an example process 900 that can be used to generate a medical alert rule. In general a graphical user interface, such as graphical user interface 200 (FIG. 2) can be used to generate a medical alert rule. In general, the process 900 is described in relation to a server 112 (FIG. 1) that is configured to perform the process 900, although other systems may be configured to perform process 900.

In operation, the server 112 accesses (910) information indicative of a question to be answered by a medical patient. In an example, the information indicative of a question to be answered can include at least some of the information shown with respect to FIG. 2, including a medical alert name. In some implementations, the question can be included in a medical assessment questionnaire of a medical service provider.

The server 112 receives (920) information indicative of a selection of one or more triggering events for answers to the question. In an example, the information indicative of a selection of one or more triggering events can include at least some of the information shown with respect to FIG. 2, including a type of trigger alert (e.g., score or alert), and a trigger (e.g., a score threshold or a particular answer to a question), and so forth. In some implementations, a triggering event can specify that the medical service provider has specified that a particular answer to the question is unacceptable and requires that the medical service provider be notified of the unacceptable answer.

The server 112 can generate (930), for the question, a medical alert rule. In some implementations, the medical alert rule can include instructions to perform one or more operations. In an example, the medical alert rule can include an instruction for receiving an answer of the medical patient to the question. In another example, the medical alert rule can include an instruction for detecting, based on contents of the received answer, the triggering event for the question. In another example, the medical alert rule can include an instruction for generating, based on detection of the triggering event, a medical questionnaire alert to notify the medical service provider that the medical patient has answered the question with the answer that is defined as being unacceptable. In a particular, a medical questionnaire alert can be presented to a medical professional using any of graphical user interfaces 400 (FIG. 4), 500 (FIG. 5), 600 (FIG. 6), and 700 (FIG. 7), as described above.

In some implementations, when performing process 900, the server 112 can also receive the answer of the medical patient to the question. In an example, the server 112 can receive the answer of the medical patient to the question using a graphical user interface 300 (FIG. 3) or 800 (FIG. 8) being presented in a client device 102 or 108 (FIG. 1), such as a tablet device 810. Following receipt of the answer, the server 112 can also execute the medical alert rule. In an example, the server 112 can execute a medical alert rule that specifies when an answer to a particular question is acceptable and when an answer to a particular question is unacceptable. In another example, the server 112 can execute a medical rule that specifies when an aggregated score for multiple questions in a medical assessment questionnaire is below a threshold score.

The server 112 can also detect, based on contents of the answer and based on execution of the medical alert rule, the triggering event that the answer of the medical patient is unacceptable and requires that the medical service provider be notified of the unacceptable answer. In an example, when a particular answer matches an answer included in or otherwise associated with the medical alert rule, the particular answer may cause the triggering event to occur to identify the answer as being unacceptable.

The server 112 can also generate, based on detection of the triggering event, the medical questionnaire alert to notify the medical service provider that the medical patient has answered the question with the answer that is defined as being unacceptable. In an example, and in response, the server 112 may generate a notification (e.g., the notifications described above in reference to FIG. 7) that may cause a medical professional to perform a particular action. The server 112 can also store, in a data repository, the medical questionnaire alert in association with information that identifies the medical patient who is associated with the medical questionnaire alert. In an example, the server 112 can store the alert in a data repository 114 (FIG. 1).

In some implementations, the medical patient can be a first medical patient. In an example, the server 112 can also access appointment information for the medical service provider, with the accessed appointment information specifying one or more appointments that are scheduled with the medical service provider. For an appointment that is scheduled with the medical service provider, the server 112 can determine a second medical patient who is associated with the appointment. The server 112 can also determine a generated medical questionnaire alert for the second medical patient. Using the accessed appointment information, the server 112 can generate information for an appointment graphical user interface. When rendered on a display device, the appointment graphical user interface can include one or more first visual representations of the one or more appointments that are scheduled with the medical service provider and a second visual representation of the generated medical questionnaire alert for the second medical patient.

In a particular example, the server 112 can generate information for an appointment graphical user interface that is substantially similar to graphical user interface 400 (FIG. 4), but includes at least a first medical patient and a second medical patient in the results region 408. In some implementations, the second visual representation is associated in the graphical user interface with the one of the one or more first visual representations that represents the appointment of the second medical patient. In an example, the second visual representation can alert the medical service provider that the second medical patient has an appointment with the medical service provider and that the second medical patient has a medical issue to be addressed by the medical service provider.

As another example, the server 112 can access patient profile information for a second medical patient. The server 112 can also identify a medical questionnaire alert for the second medical patient. The server 112 can also generate information for a patient profile graphical user interface that when rendered on a display device includes a first visual representation of the patient profile information and a second visual representation of the identified medical questionnaire alert for the second medical patient and a status of the medical questionnaire alert. In an example, the status specifies whether the alert is pending or resolved. In a particular example, the second visual representation is juxtaposed to the first visual representation in the patient profile graphical user interface.

In some implementations, the server 112 can also access information indicative of a plurality of medical questionnaire alerts for the medical service provider. The server 112 can also aggregate the plurality of medical questionnaire alerts together. In an example, the server 112 can generate information for an alert management graphical user interface that when rendered on a display device includes visual representations of the aggregated plurality of medical questionnaire alerts.

Figure 10:
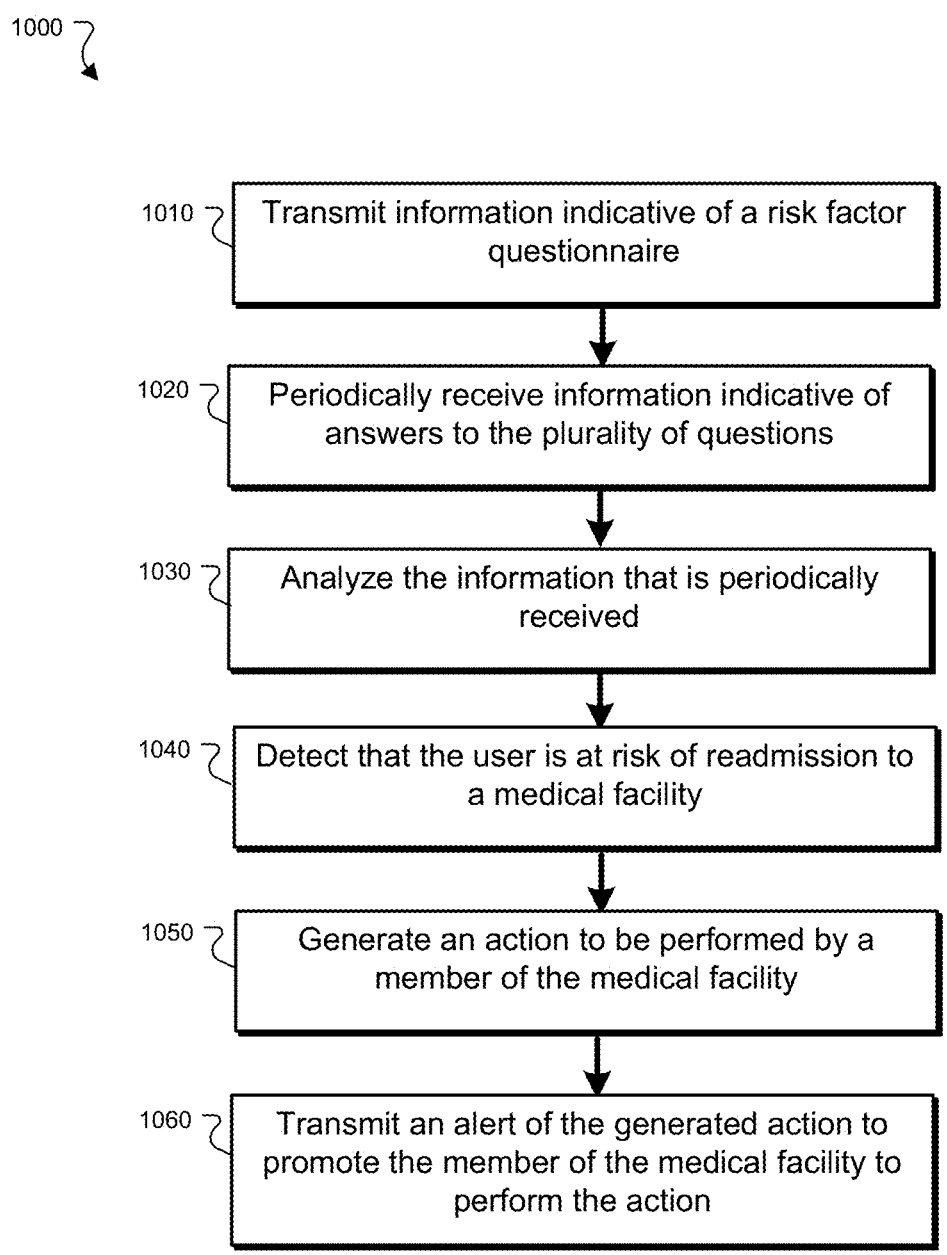
FIG. 10 is a flow chart of an example process that can be used to generate information for an action to be performed by a member of a medical facility.

FIG. 10 is a flow chart of an example process 1000 that can be used to generate an action to be performed by a member of a medical facility. In general, the action is associated with a medical questionnaire alert. In general, the medical questionnaire alert can be based on one or more answers provided by a medical patient. In general, if the member of the medical facility does not perform the action in a timely fashion, the action may be escalated to another member of the medical facility. In general, the process 1000 is described in relation to a server 112 (FIG. 1) that is configured to perform the process 1000, although other systems may be configured to perform process 1000.

In operation, the server 112 transmits (1010), to a client computing device associated with a user, information indicative of a risk factor questionnaire. In an example, the risk factor questionnaire can include a plurality of questions regarding risk factors of a medical procedure performed on the user. In a particular example, the server 112 can transmit a questionnaire that looks substantially similar to the questionnaire presented in the graphical user interface 800 (FIG. 8) presented by the tablet device 810.

The server 112 periodically receives (1020), from the client computing device, information indicative of answers to the plurality of questions regarding the risk factors of the medical procedure. In an example, as the user (e.g., a medical patient) of the tablet device 810 (FIG. 8) selects answers, the answers can be transmitted by the tablet device 810 and received by the server 112 (FIG. 1).

The server 112 analyzes (1030), by one or more processing devices and over a predefined period of time, the information that is periodically received. In an example, the server 112 (FIG. 1) can analyze the received answers to determine at least one of a trend formed by the received answers and unacceptable answers to one or more of the questions.

The server 112 detects (1040), by the one or more processing devices and based on analyzing, that the user is at risk of readmission to a medical facility. As an example, the server 112 (FIG. 1) can detect an increase in a severity of a medical condition of the user during one or more time intervals in predefined period of time, relative to a severity of the medical condition during other time intervals in the predefined period of time. In some implementations, the server 112 can determine that the detected increase exceeds a threshold level. Based on determining that the detected increase exceeds the threshold level, the server 112 detects that the user is at risk of readmission to a medical facility comprises. That is, when the increase in a severity of a medical condition exceeds the threshold level, a patient is at increased risk of being readmitted to the hospital. Accordingly, system 112 implements the techniques described herein to reduce the risk of readmission, e.g., by having the alerts addressed by medical staff and personnel to prevent the patient from returning to the hospital or medical facility.

The server 112 generates (1050), by the one or more processing devices, an action to be performed by a member of the medical facility, with performance of the action reducing the risk of readmission relative to other risks of readmission that are independent of performance of the action. In a particular example, the server 112 may generate one or more actions, such one or more presented in actions region 744 (FIG. 7).

The server 112 transmits (1060), to a client computing device associated with the medical facility, an alert of the generated action to promote the member of the medical facility to perform the action. In some implementations, the server 112 can generate information for a graphical user interface. In an example, the rendered graphical user interface can include a first visual indicator of first answers of the user to a first question pertaining to a first one of the risk factors, with the first answers being displayed in the graphical user interface over a period of time. In an example, the rendered graphical user interface can also include a second visual indicator of second answers of the user to a second question pertaining to a second one of the risk factors, with the second answers being displayed in the graphical user interface over the period of time. In a particular example, a graphical user interface 700 (FIG. 7) can be rendered based on the information generated by the server 112. In some implementations, the server 112 can export the generated information for the graphical user interface, with the information being exported to a client computing device associated with one or more of a government entity, a history, an electronic medical record entity, and a business intelligence entity. In some implementations, a visual indicator of the alert and an explanation of the reason for the alert. In an example, a text region 722 (FIG. 7) can be presented in the graphical user interface 700 that provides an explanation for the reason for the alert.

In some implementations, the server 112 (FIG. 1) can wait, for a predefined period of time, for information specifying that the member of the medical facility has performed the action. After the predefined period of time has elapsed, the server 112 can escalate the alert to one or more other members of the medical facility. In an example, the alert is escalated by notifying the one or more other members of the medical facility.

In some implementations, the risk of readmission is associated with a particular risk factor from the risk factors. In an example, the information indicative of answers to the plurality of questions can include first information. In an example, the server 112 can receive information specifying that the member of the medical facility has performed the action. The server 112 can also specify that the member of the medical facility has performed the action following receipt of the information. The server 112 can periodically receive, from the client computing device, second information indicative of answers to questions regarding the particular risk factor. The server 112 can also analyze, by one or more processing devices and over a predefined period of time, the second information in comparison to the first information.

In some implementations, the server 112 can determine, by the one or more processing devices and based on analyzing, that performance of that action has decreased the risk of readmission relative to the risk of readmission prior to performance of the action.

In addition, or alternatively, the server 112 can determine, by the one or more processing devices and based on analyzing, that the risk of readmission following performance of the action is unchanged. In an example, the server 112 may generate, by the one or more processing devices, another action to be performed by a member of the medical facility, with performance of the other action reducing the risk of readmission relative to other risks of readmission that are independent of performance of the other action. In a particular example, if a medical patient's pain has not subsided after administration of a pain-relieving drug, an action to schedule a physical visit may be generated by the server 112.

In addition, or alternatively, the server 112 may also generate, by the one or more processing devices, another action to be performed by a member of the medical facility, with performance of the other action reducing the risk of readmission relative to other risks of readmission that are independent of performance of the other action.

Figure 11:
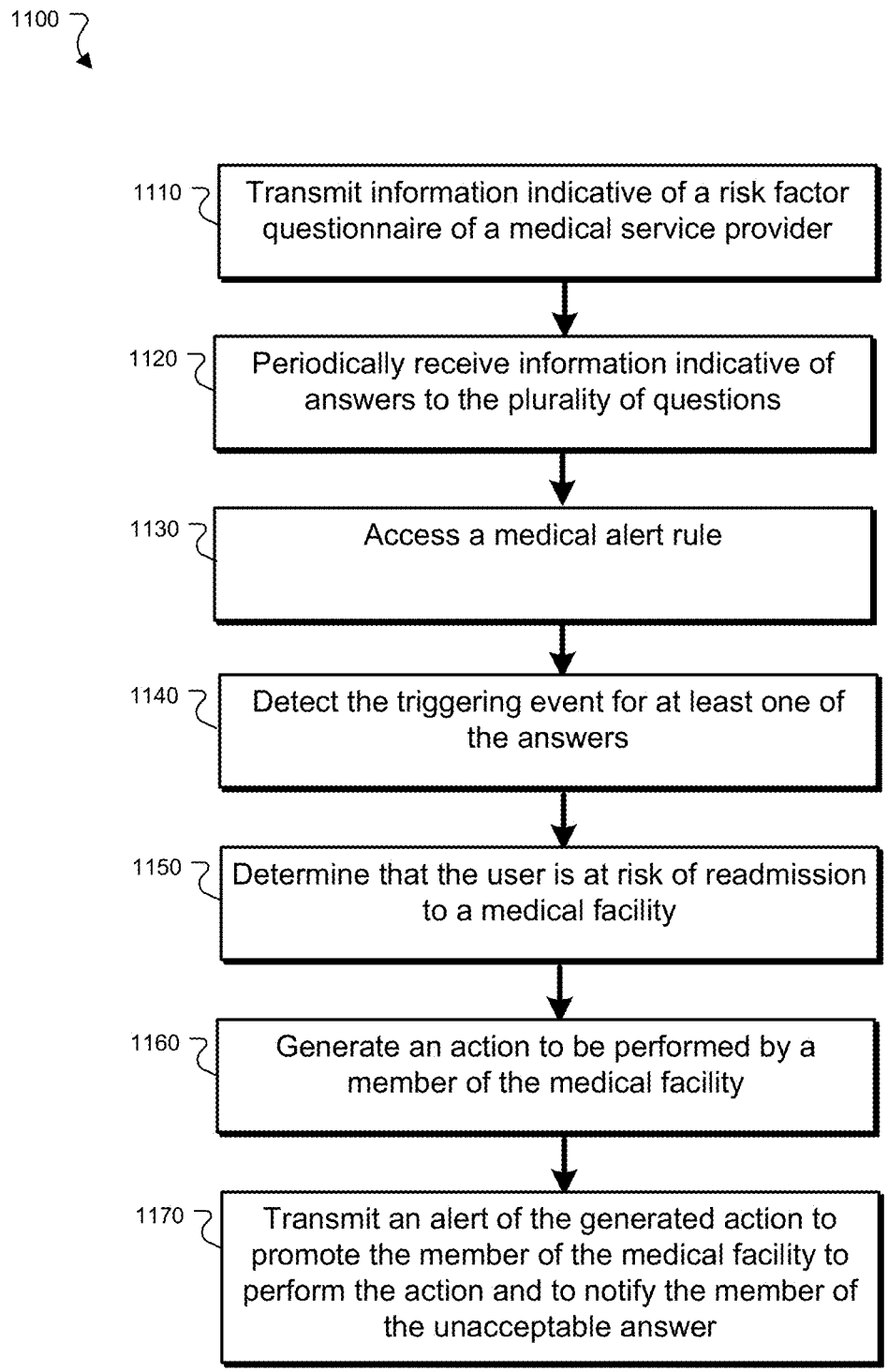
FIG. 11 is a flow chart of another example process that can be used to generate information for an action to be performed by a member of the medical facility.

FIG. 11 is a flow chart of another example process 1100 that can be used to generate an action to be performed by a member of the medical facility. In general information that corresponds to answers provided by a medical patient can be compared to a medical alert rule. The medical alert rule may trigger an event. When an event is triggered, a risk for readmission can be determined. If there is a risk for readmission, an action can be taken that—when performed by a member of a medical facility—may reduce the risk of readmission. In general, the process 1100 is described in relation to a server 112 (FIG. 1) that is configured to perform the process 1100, although other systems may be configured to perform process 1100.

In operation, the server 112 transmits (1110), to a client computing device associated with a medical patient, information indicative of a risk factor questionnaire of a medical service provider, with the risk factor questionnaire comprising a plurality of questions regarding risk factors of the medical patient. In an example, the server 112 can transmit a questionnaire that is substantially similar to the questionnaire presented in the graphical user interface 800 (FIG. 8) presented by the tablet device 810.

The server 112 may periodically receive (1120), from the client computing device, information indicative of answers to the plurality of questions regarding the risk factors of the medical procedure. In an example, as the user (e.g., a medical patient) of the tablet device 810 (FIG. 8) selects answers, the answers can be transmitted by the tablet device 810 and received by the server 112 (FIG. 1).

The server 112 can access (1130), from a data repository, a medical alert rule. In an example, the server can access the data repository 114. In some implementations, the medical alert rule can specify one or more instructions for detecting a triggering event. In an example, the triggering event can specify that the medical service provider has specified that a particular answer to a question is unacceptable and requires that the medical service provider be notified of the unacceptable answer. In a particular example, the triggering event can be configured using a graphical user interface, such as graphical user interface 200 (FIG. 2).

The server 112 can detect (1140), by one or more processing devices in the received information indicative of answers, the triggering event for at least one of the answers. In some implementations, the triggering event may specify that the medical service provider has specified that the at least one of the answers to the question is unacceptable and requires that the medical service provider be notified of the unacceptable answer. As a result, as an example, the server 112 can detect that a received answer matches an unacceptable answer the particular question.

The server 112 can determine (1150), based on detection of the triggering event, that the user is at risk of readmission to a medical facility. In an example, one or more answers to questions in a risk factor questionnaire can be indicative of one or more medical complications. Based on the answers provided by the medical patient, one or more medical complications can be determined, some of these complications may be indicative of an increased risk of readmission to a medical facility. In a particular example, combinations of post-operative fever, pain, swelling of the operated on area, and other symptoms may be indicative of an infection that may increase the risk of readmission the medical facility.

The server 112 can generate (1160), by the one or more processing devices, an action to be performed by a member of the medical facility, with performance of the action reducing the risk of readmission relative to other risks of readmission that are independent of performance of the action. In an example, the member of the medical facility can prescribe a medication or perform some other action that reduces the risk of readmission.

The server 112 can transmit (1170), to a client computing device associated with the medical facility, an alert of the generated action to promote the member of the medical facility to perform the action and to notify the member of the unacceptable answer. In an example, the server 112 can transmit information that can be used to render a graphical user interface, such as graphical user interface 700 (FIG. 7).

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method, comprising:

accessing, by a computer system, a first relational data structure that includes fields structuring information indicative of a question to be answered by a user of a user device, with the question being included in a medical assessment questionnaire of a medical service provider;

receiving, by the computer system, a second relational data structure that includes fields structuring information indicative of a selection of one or more triggering events for answers to the question, wherein the triggering event is configured to detect that a particular answer to the question includes an acceptable answer that is trending in an unacceptable direction without exceeding a predetermined threshold from an acceptable answer to an unacceptable answer and requires that the medical service provider be notified of the particular answer;

executing computer program code that correlates, by the computer system, (i) the accessed information that is structured by the fields of the first relational data structure and indicative of a question to be answered by a user of the user device, (ii) the received information that is structured by the fields of the second relational data structure and indicative of the selected one or more triggering events, and (iii) information that is structured by fields of a third relational data structure and indicative one or more answers to the question;

executing computer program code that modifies, by the computer system and for the question, a fourth relational data structure to include a fifth relational data structure that includes one or more fields structuring information that establishes a medical alert rule using the correlated information, with the one or more fields of the fifth relational data structure structuring information that defines executable program code comprising instructions to perform operations that, when executed by the computer system, instruct the computer system to:

detect, based on an answer received from the user, an occurrence of the triggering event for the question; and generate, based on the detection of the occurrence of the triggering event, a sixth relational data structure that includes fields structuring information that includes rendering data that, when rendered by a second user device, causes the second user device to render a medical questionnaire alert for output on a display of the second user device that notifies the medical service provider that the answer received from the user includes the particular answer that was determined to include an acceptable answer that is trending in an unacceptable direction without exceeding a predetermined threshold from an acceptable answer to an unacceptable answer, storing, by the computer system, the fifth relational data structure that includes the one or more fields structuring information that establishes the medical alert rule and includes one or more fields structuring the defined executable program code in a database maintained in a memory device, wherein storing the generated fifth relational data structure comprises storing the fifth relational data structure in association with a key value that identifies the user associated with the medical alert rule;

receiving, by the computer system, a seventh relational data structure that includes one or more fields structuring first information indicative of information provided from the user after generation of the fifth relational data structure that includes one or more fields structuring information that establishes the medical alert rule, wherein the first information includes (i) a key value identifying the user and (ii) information representing the particular answer of the user to the question;

following receipt of the seventh relational data structure that includes one or more fields structuring the first information that includes (i) the key value identifying the user and (ii) the information representing the particular answer, determining, by the computer system, to execute the medical alert rule based on the key value identifying the user and the information representing the particular answer, wherein executing the medical alert rule comprises executing the defined executable program code that is structured by the fifth relational data structure and stored in the memory device;

detecting, by the computer system based on execution of the defined executable code that is structured by the fifth relational data structure, an occurrence of the triggering event indicating that the particular answer of the user includes an acceptable answer that is trending in an unacceptable direction without exceeding a predetermined threshold from an acceptable answer to an unacceptable answer and requires that the medical service provider be notified of the unacceptable answer;

generating, by the computer system and based on detection of the occurrence of the triggering event, the sixth relational data structure that includes fields structuring information that includes rendering data that, when rendered by the second user device, causes the second user device to render a medical questionnaire alert for output on a display of the second user device that notifies the medical service provider that the user has answered the question with the answer that is defined as including an acceptable answer that is trending in an unacceptable direction, and transmitting, by the computer system, the generated sixth relational data structure to the second user device.

2. The computer-implemented method of claim 1, wherein the user comprises a first user, and wherein the method further comprises:

accessing appointment information for the medical service provider, with the accessed appointment information specifying one or more appointments that are scheduled with the medical service provider;

for an appointment that is scheduled with the medical service provider, determining a second user who is associated with the appointment;

determining a generated medical questionnaire alerts for the second user;

using the accessed appointment information,
generating information for an appointment graphical user interface that when rendered on a display device comprises:
one or more first visual representations of the one or more appointments that are scheduled with the medical service provider; and
a second visual representation of the generated medical questionnaire alert for the second user;
wherein the second visual representation is associated in the graphical user interface with the one of the one or more first visual representations that represents the appointment of the second user, to alert the medical service provider that the second user has an appointment with the medical service provider and that the second user has a medical issue to be addressed by the medical service provider.

3. The computer-implemented method of claim 1, wherein the user comprises a first user, and wherein the method further comprises:

accessing user profile information for a second user;
identifying a medical questionnaire alert for the second user;
generating information for a user profile graphical user interface that when rendered on a display device comprises:
a first visual representation of the user profile information; and
a second visual representation of the identified medical questionnaire alert for the second and a status of the medical questionnaire alert, with the status specifying whether the alert is pending or resolved;
wherein the second visual representation is juxtaposed to the first visual representation in the user profile graphical user interface.

4. The computer-implemented method of claim 1, further comprising:

accessing information indicative of a plurality of medical questionnaire alerts for the medical service provider;
aggregating the plurality of medical questionnaire alerts together;
generating information for an alert management graphical user interface that when rendered on a display device comprises:
visual representations of the aggregated plurality of medical questionnaire alerts.

5. A system comprising:
one or more computers and one or more storage devices storing instructions that are operable, when executed by the one or more computers, to cause the one or more computers to perform operations comprising:
accessing, by a computer system, a first relational data structure that includes fields structuring information indicative of a question to be answered by a user of a user device, with the question being included in a medical assessment questionnaire of a medical service provider;
receiving, by the computer system, a second relational data structure that includes fields structuring information indicative of a selection of one or more triggering events for answers to the question, wherein the triggering event is configured to detect that a particular answer to the question includes an acceptable answer that is trending in an unacceptable direction without exceeding a predetermined threshold from an acceptable answer to an unacceptable answer and requires that the medical service provider be notified of the particular answer;
executing computer program code that correlates, by the computer system, (i) the accessed information that is structured by the fields of the first relational data structure and indicative of a question to be answered by a user of the user device, (ii) the received information that is structured by the fields of the second relational data structure and indicative of the selected one or more triggering events, and (iii) information that is structured by fields of a third relational data structure and indicative one or more answers to the question;

executing computer program code that modifies, by the computer system and for the question, a fourth relational data structure to include a fifth relational data structure that includes one or more fields structuring information that establishes a medical alert rule using the correlated information, with the one or more fields of the fifth relational data structure structuring information that defines executable program code comprising instructions to perform operations that, when executed by the computer system, instruct the computer system to:

detect, based on an answer received from the user, an occurrence of the triggering event for the question; and generate, based on the detection of the occurrence of the triggering event, a sixth relational data structure that includes fields structuring information that includes rendering data that, when rendered by a second user device, causes the second user device to render a medical questionnaire alert for output on a display of the second user device that notifies the medical service provider that the answer received from the user includes the particular answer that was determined to include an acceptable answer that is trending in an unacceptable direction without exceeding a predetermined threshold from an acceptable answer to an unacceptable answer;

storing, by the computer system, the fifth relational data structure that includes the one or more fields structuring information that establishes the medical alert rule and includes one or more fields structuring the defined executable program code in a database maintained in a memory device, wherein storing the generated fifth relational data structure comprises storing the fifth relational data structure in association with a key value that identifies the user associated with the medical alert rule;

receiving, by the computer system, a seventh relational data structure that includes one or more fields structuring first information indicative of information provided from the user after generation of the fifth relational data structure that includes one or more fields structuring information that establishes the medical alert rule, wherein the first information includes (i) a key value identifying the user and (ii) information representing the particular answer of the user to the question;

following receipt of the seventh relational data structure that includes one or more fields structuring the first information that includes (i) the key value identifying the user and (ii) the information representing the particular answer, determining, by the computer system, to execute the medical alert rule based on the key value identifying the user and the information representing the particular answer, wherein executing the medical alert rule comprises executing the defined executable program code that is structured by the fifth relational data structure and stored in the memory device;

detecting, by the computer system based on execution of the defined executable code that is structured by the fifth relational data structure, an occurrence of the triggering event indicating that the particular answer of the user includes an acceptable answer that is trending in an unacceptable direction without exceeding a predetermined threshold from an acceptable answer to an unacceptable answer and requires that the medical service provider be notified of the unacceptable answer;

generating, by the computer system and based on detection of the occurrence of the triggering event, the sixth relational data structure that includes fields structuring information that includes rendering data that, when rendered by the second user device, causes the second user device to render a medical questionnaire alert for output on a display of the second user device that notifies the medical service provider that the user has answered the question with the answer that is defined as including an acceptable answer that is trending in an unacceptable direction; and transmitting, by the computer system, the generated sixth relational data structure to the second user device.

6. The system of claim 5, wherein the user comprises a first user, and wherein the operations further comprise:

accessing appointment information for the medical service provider, with the accessed appointment information specifying one or more appointments that are scheduled with the medical service provider;

for an appointment that is scheduled with the medical service provider, determining a second user who is associated with the appointment;

determining a generated medical questionnaire alerts for the second user;

using the accessed appointment information,
generating information for an appointment graphical user interface that when rendered on a display device comprises:
one or more first visual representations of the one or more appointments that are scheduled with the medical service provider; and
a second visual representation of the generated medical questionnaire alert for the second user;
wherein the second visual representation is associated in the graphical user interface with the one of the one or more first visual representations that represents the appointment of the second user, to alert the medical service provider that the second user has an appointment with the medical service provider and that the second user has a medical issue to be addressed by the medical service provider.

7. The system of claim 5, wherein the user comprises a first user, and wherein the operations further comprise:

accessing user profile information for a second user;
identifying a medical questionnaire alert for the second user;
generating information for a user profile graphical user interface that when rendered on a display device comprises:
a first visual representation of the user profile information; and
a second visual representation of the identified medical questionnaire alert for the second and a status of the medical questionnaire alert, with the status specifying whether the alert is pending or resolved;
wherein the second visual representation is juxtaposed to the first visual representation in the user profile graphical user interface.

8. The system of claim 5, the operations further comprising:
   accessing information indicative of a plurality of medical questionnaire alerts for the medical service provider;
   aggregating the plurality of medical questionnaire alerts together;
   generating information for an alert management graphical user interface that when rendered on a display device comprises:
      visual representations of the aggregated plurality of medical questionnaire alerts.

9. A non-transitory computer-readable medium storing software comprising instructions executable by one or more computers which, upon such execution, cause the one or more computers to perform operations comprising:
   accessing, by a computer system, a first relational data structure that includes fields structuring information indicative of a question to be answered by a user of a user device, with the question being included in a medical assessment questionnaire of a medical service provider;
   receiving, by the computer system, a second relational data structure that includes fields structuring information indicative of a selection of one or more triggering events for answers to the question, wherein the triggering event is configured to detect that a particular answer to the question includes an acceptable answer that is trending in an unacceptable direction without exceeding a predetermined threshold from an acceptable answer to an unacceptable answer and requires that the medical service provider be notified of the particular answer;
   executing computer program code that correlates, by the computer system, (i) the accessed information that is structured by the fields of the first relational data structure and indicative of a question to be answered by a user of the user device, (ii) the received information that is structured by the fields of the second relational data structure and indicative of the selected one or more triggering events, and (iii) information that is structured by fields of a third relational data structure and indicative one or more answers to the question;
   executing computer program code that modifies, by the computer system and for the question, a fourth relational data structure to include a fifth relational data structure that includes one or more fields structuring information that establishes a medical alert rule using the correlated information, with the one or more fields of the fifth relational data structure structuring information that defines executable program code comprising instructions to perform operations that, when executed by the computer system, instruct the computer system to:
      detect, based on an answer received from the user, an occurrence of the triggering event for the question; and
      generate, based on the detection of the occurrence of the triggering event, a sixth relational data structure that includes fields structuring information that includes rendering data that, when rendered by a second user device, causes the second user device to render a medical questionnaire alert for output on a display of the second user device that notifies the medical service provider that the answer received from the user includes the particular answer that was determined to include an acceptable answer that is trending in an unacceptable direction without exceeding a predetermined threshold from an acceptable answer to an unacceptable answer,
   storing, by the computer system, the fifth relational data structure that includes the one or more fields structuring information that establishes the medical alert rule and includes one or more fields structuring the defined executable program code in a database maintained in a memory device, wherein storing the generated fifth relational data structure comprises storing the fifth relational data structure in association with a key value that identifies the user associated with the medical alert rule;
   receiving, by the computer system, a seventh relational data structure that includes one or more fields structuring first information indicative of information provided from the user after generation of the fifth relational data structure that includes one or more fields structuring information that establishes the medical alert rule, wherein the first information includes (i) a key value identifying the user and (ii) information representing the particular answer of the user to the question;
   following receipt of the seventh relational data structure that includes one or more fields structuring the first information that includes (i) the key value identifying the user and (ii) the information representing the particular answer, determining, by the computer system, to execute the medical alert rule based on the key value identifying the user and the information representing the particular answer, wherein executing the medical alert rule comprises executing the defined executable program code that is structured by the fifth relational data structure and stored in the memory device;
   detecting, by the computer system based on execution of the defined executable code that is structured by the fifth relational data structure, an occurrence of the triggering event indicating that the particular answer of the user includes an acceptable answer that is trending in an unacceptable direction without exceeding a predetermined threshold from an acceptable answer to an unacceptable answer and requires that the medical service provider be notified of the unacceptable answer;
   generating, by the computer system and based on detection of the occurrence of the triggering event, the sixth relational data structure that includes fields structuring information that includes rendering data that, when rendered by the second user device, causes the second user device to render a medical questionnaire alert for output on a display of the second user device that notifies the medical service provider that the user has answered the question with the answer that is defined as including an acceptable answer that is trending in an unacceptable direction; and
   transmitting, by the computer system, the generated sixth relational data structure to the second user device.

10. The computer-readable medium of claim 9, wherein the user comprises a first user, and wherein the operations further comprise:
   accessing appointment information for the medical service provider, with the accessed appointment information specifying one or more appointments that are scheduled with the medical service provider;
   for an appointment that is scheduled with the medical service provider, determining a second user who is associated with the appointment;
   determining a generated medical questionnaire alerts for the second user;
   using the accessed appointment information, generating information for an appointment graphical user interface that when rendered on a display device comprises:
  one or more first visual representations of the one or more appointments that are scheduled with the medical service provider; and
  a second visual representation of the generated medical questionnaire alert for the second user;
  wherein the second visual representation is associated in the graphical user interface with the one of the one or more first visual representations that represents the appointment of the second user, to alert the medical service provider that the second user has an appointment with the medical service provider and that the second user has a medical issue to be addressed by the medical service provider.

11. The computer-readable medium of claim 9, wherein the user comprises a first user, and wherein the operations further comprise:
  accessing user profile information for a second user;
  identifying a medical questionnaire alert for the second user;
  generating information for a user profile graphical user interface that when rendered on a display device comprises:
    a first visual representation of the user profile information; and
    a second visual representation of the identified medical questionnaire alert for the second and a status of the medical questionnaire alert, with the status specifying whether the alert is pending or resolved;
  wherein the second visual representation is juxtaposed to the first visual representation in the user profile graphical user interface.

12. The computer-readable medium of claim 9, the operations further comprising:
  accessing information indicative of a plurality of medical questionnaire alerts for the medical service provider;
  aggregating the plurality of medical questionnaire alerts together;
  generating information for an alert management graphical user interface that when rendered on a display device comprises:
    visual representations of the aggregated plurality of medical questionnaire alerts.

* * * * *